(12) United States Patent
Newell et al.

(10) Patent No.: US 8,450,090 B2
(45) Date of Patent: May 28, 2013

(54) COMPOSITIONS AND METHODS FOR PROMOTING FATTY ACID PRODUCTION IN PLANTS

(75) Inventors: Martha Karen Newell, Holland, TX (US); Sandy Berry-Lowe, Colorado Springs, CO (US); Richard Tobin, Aurora, CO (US); Odbert Triplett, Little Rock, AR (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 178 days.

(21) Appl. No.: 12/574,694

(22) Filed: Oct. 6, 2009

(65) Prior Publication Data

US 2011/0078946 A1    Apr. 7, 2011

(51) Int. Cl.
*C10L 1/19* (2006.01)
*C01B 3/32* (2006.01)
*C12P 7/62* (2006.01)
*C12N 1/12* (2006.01)
*C12N 1/14* (2006.01)

(52) U.S. Cl.
USPC ............. 435/135; 44/388; 252/375; 504/149; 435/254.1; 435/257.1

(58) Field of Classification Search
None
See application file for complete search history.

(56) References Cited

U.S. PATENT DOCUMENTS

| 4,205,075 | A | 5/1980 | Baldwin et al. |
| 4,441,918 | A | 4/1984 | Rehberg |
| 4,724,234 | A | 2/1988 | Cone, Jr. |
| 4,935,450 | A | 6/1990 | Cone, Jr. |
| 5,163,992 | A | 11/1992 | Rentzea et al. |
| 5,627,132 | A | 5/1997 | LeBeau |
| 6,005,167 | B1 | 12/1999 | Van Tunen et al. |
| 6,166,291 | B1 | 12/2000 | Bidney et al. |
| 6,184,440 | B1 | 2/2001 | Shoseyov et al. |
| 6,187,571 | B1 | 2/2001 | Pignard et al. |
| 6,204,437 | B1 | 3/2001 | Grierson et al. |
| 6,670,330 | B1 | 12/2003 | Lampidis et al. |
| 7,105,718 | B2 * | 9/2006 | Newell et al. ................. 800/276 |
| 7,160,865 | B2 | 1/2007 | Lampidis et al. |
| 7,510,710 | B2 | 3/2009 | Newell et al. |
| 2001/0038805 | A1 | 11/2001 | Hamilton et al. |
| 2002/0039971 | A1 | 4/2002 | Hayashi et al. |
| 2002/0123430 | A1 | 9/2002 | Xu et al. |
| 2003/0022793 | A1 | 1/2003 | Ring et al. |
| 2003/0150022 | A1 | 8/2003 | Newell et al. |
| 2003/0224939 | A1 | 12/2003 | Miles |
| 2004/0029961 | A1 | 2/2004 | Von Krosigk et al. |
| 2004/0096471 | A1 | 5/2004 | Hakala et al. |
| 2004/0097372 | A1 | 5/2004 | Abraham et al. |
| 2004/0167079 | A1 | 8/2004 | Tidmarsh |
| 2004/0244078 | A1 * | 12/2004 | Baker et al. ................. 800/281 |
| 2005/0020682 | A1 | 1/2005 | Newell et al. |
| 2005/0043250 | A1 | 2/2005 | Lampidis et al. |
| 2005/0079227 | A1 | 4/2005 | Tate |
| 2005/0145475 | A1 | 7/2005 | Okada et al. |
| 2006/0014641 | A1 | 1/2006 | Zaghmout |
| 2006/0025351 | A1 | 2/2006 | Lampidis et al. |
| 2006/0247199 | A1 | 6/2006 | Newell et al. |
| 2007/0032383 | A1 | 2/2007 | Newell |
| 2007/0161832 | A1 | 7/2007 | Myllyoja et al. |
| 2007/0249500 | A1 | 10/2007 | Cigler et al. |
| 2009/0258064 | A1 | 10/2009 | Newell et al. |
| 2009/0288337 | A1 | 11/2009 | Picataggio et al. |
| 2010/0112649 | A1 | 5/2010 | Willson et al. |
| 2010/0184710 | A1 | 7/2010 | Newell |
| 2010/0297749 | A1 | 11/2010 | Aravanis et al. |

FOREIGN PATENT DOCUMENTS

| WO | WO 95/19765 A1 | 7/1995 |
| WO | WO 01/64246 A2 | 9/2001 |
| WO | WO 03/037323 A2 | 5/2003 |
| WO | WO 2004/062604 A2 | 7/2004 |
| WO | WO 2004/110255 A2 | 12/2004 |
| WO | WO 2006/108276 A1 | 10/2006 |
| WO | WO 2006/119355 A2 | 11/2006 |
| WO | WO 2008/119082 A2 | 10/2008 |
| WO | WO 2010/123903 A1 | 10/2010 |

OTHER PUBLICATIONS

Lv et al. (Energy Conserv. Manag. (2007) 48: 1132-1139.*
Miao et al. (2006) Biores. Technol. 97: 841-846.*
Demirbas et al. (2007) Prog. Energy Combust. Sci. 33:1-18.*
Minowa et al. (1995) Fuel 74: 1735-1738.*
Miao et al. (2004) J. Anal Appl. Pyrolysis 71: 855-863.*
Goepfert et al. (2007) Curr. Opin. Plant Biol. 10: 245-251.*
Horn et al., Etomoxir, a fatty acid oxidation inhibitor, increases food intake and reduces hepatic energy status in rats. Physiol Behav. Mar. 2004;81(1):157-62.
Abdel-Aleem et al., Regulation of glucose utilization during the inhibition of fatty acid oxidation in rat myocytes. Horm Metab Res. Feb. 1994;26(2):88-91.
Blatti et al., Manipulating Fatty Acid Biosynthesis in Microalgae for Biofuel through Protein-Protein Interactions. PLoS One. 2012;7(9):e42949. doi: 10.1371/journal.pone.0042949. Epub Sep. 13, 2012.
Brandalise et al., Overexpression of plant uncoupling mitochondrial protein in transgenic tobacco increases tolerance to oxidative stress. J Bioenerg Biomembr. Jun. 2003;35(3):203-9.
Cabrero et al., Etomoxir, sodium 2-[6-(4-chlorophenoxy)hexyl]oxirane-2-carboxylate, up-regulates uncoupling protein-3 mRNA levels in primary culture of rat preadipocytes. Biochem Biophys Res Commun. Sep. 16, 1999;263(1):87-93.
Certik et al., Biosynthesis and regulation of microbial polyunsaturated fatty acid production. J Biosci Bioeng. 1999;87(1):1-14.
Chamovitz et al., The molecular basis of resistance to the herbicide norflurazon. Plant Mol Biol. Jun. 1991;16(6):967-74. Abstract only.
Friedman et al., Integrated metabolic control of food intake. Brain Res Bull. Dec. 1986;17(6):855-9.
Hermesh et al., Mitochondria uncoupling by a long chain fatty acyl analogue. J Biol Chem. Feb. 13, 1998;273(7):3937-42.
Higgins et al., The relationship between glycolysis, fatty acid metabolism and membrane integrity in neonatal myocytes. J Mol Cell Cardiol. Jun. 1981;13(6):599-615.

(Continued)

*Primary Examiner* — David T Fox
*Assistant Examiner* — Steven Bernacki
(74) *Attorney, Agent, or Firm* — Wolf, Greenfield & Sacks, P.C.

(57) ABSTRACT

The invention relates to methods and products for producing fatty acids by manipulating metabolic function in plants and fungus. The fatty acids generated according to the invention may be useful in the production of biofuels.

13 Claims, 11 Drawing Sheets

OTHER PUBLICATIONS

Khozin et al., Elucidation of the Biosynthesis of Eicosapentaenoic Acid in the Microalga Porphyridium cruentum.Plant Physiol. 1997. 114: 223-230.

Koop et al., Continuous bioluminescent monitoring of cytoplasmic ATP in single isolated rat hepatocytes during metabolic poisoning. Biochem J. Oct. 1, 1993;295 (Pt 1):165-70.

Kowaltowski et al., Activation of the potato plant uncoupling mitochondrial protein inhibits reactive oxygen species generation by the respiratory chain. FEBS Lett. Mar. 27, 1998;425(2):213-6.

Kuhajda et al., Synthesis and antitumor activity of an inhibitor of fatty acid synthase. Proc Natl Acad Sci USA. Mar. 28, 2000;97(7):3450-4.

Laloi et al., A plant cold-induced uncoupling protein. Nature. Sep. 11, 1997;389(6647):135-6.

Newell et al., Studies with glycolysis-deficient cells suggest that production of lactic acid is not the only cause of tumor acidity, 1993, Proc. Natl. Acad. Sci., vol. 90, pp. 1127-1131.

Radakovits et al., Genetic engineering of algae for enhanced biofuel production. Eukaryot Cell. Apr. 2010;9(4):486-501. Epub Feb. 5, 2010.

Ricquier et al., The uncoupling protein homologues: UCP1, UCP2, UCP3, StUCP and AtUCP. Biochem J. Jan. 15, 2000;345 Pt 2:161-79. Review.

Samec et al., Skeletal muscle UCP3 and UCP2 gene expression in response to inhibition of free fatty acid flux through mitochondrial beta-oxidation. Pflugers Arch. Sep. 1999;438(4):452-7.

Schulz, Inhibitors of fatty acid oxidation. Life Sci. Apr. 13, 1987;40(15):1443-9.

Stacpoole et al., "Clinical Pharmacology and Toxicology of Dichloroacetate" Environmental Health Perspectives, vol. 106, Supplement 4, Aug. 1998.

Stamper et al., Metabolic fuel availability influences thermoregulation in deer mice (*Peromyscus maniculatus*). Physiol Behav. Apr. 1997;61(4):521-4.

Trebst et al., Role of carotene in the rapid turnover and assembly of photosystem II in *Chlamydomonas reinhardtii*. FEBS Lett. Jan. 6, 1997;400(3):359-62. Abstract only.

Venkatesan et al., Dexamethasone-induced impairment in skeletal muscle glucose transport is not reversed by inhibition of free fatty acid oxidation. Metabolism. Jan. 1996;45(1):92-100.

Vidal-Puig, Uncoupling expectations. Nat Genet. Dec. 2000;26(4):387-8.

Watanabe et al., AtUCP2: a novel isoform of the mitochondrial uncoupling protein of *Arabidopsis thaliana*. Plant Cell Physiol. Nov. 1999;40(11):1160-6.

Zhekisheva et al, Inhibition of Astaxanthin Synthesis Under High Irradiance Does Not Abolish Triacylglycerol Accumulation in the Green Alga *Haematococcus pluvialis* (Chlorophyceae). J. Phycol. 2005;41:819-826.

* cited by examiner

Schizochytrium Treated with Oxamate

FL1 represents fluorescence of Lysosensor stain as a function of fatty acid content Schizochytrium 168 Hours Post Treatment

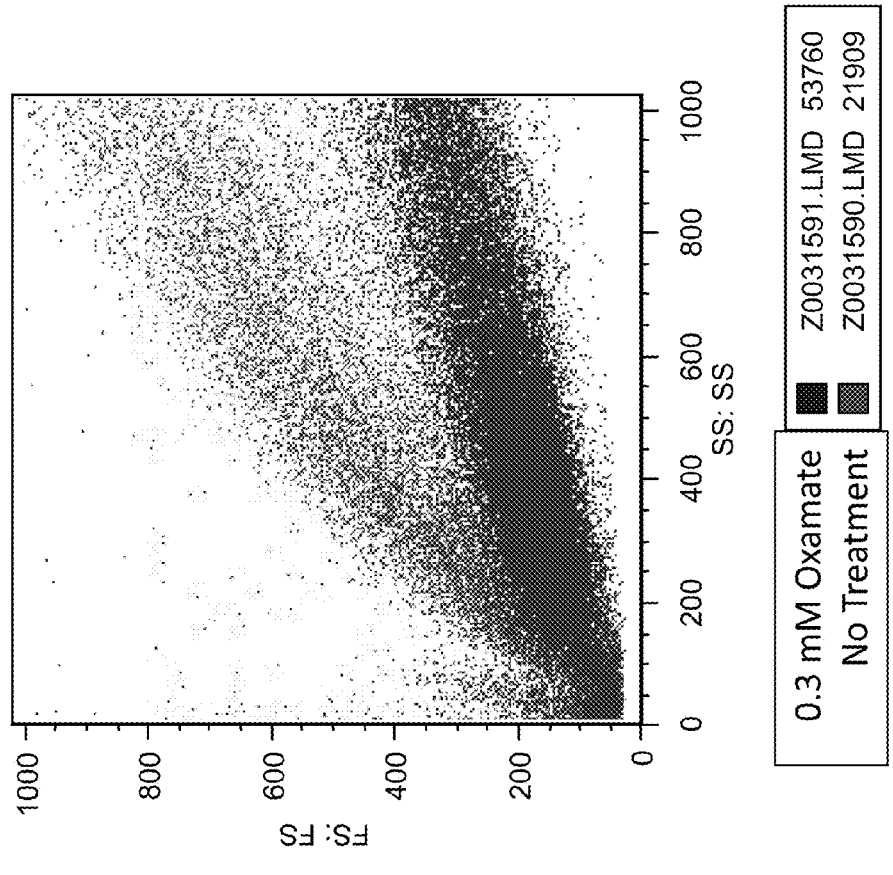

COMPOSITIONS AND METHODS FOR PROMOTING FATTY ACID PRODUCTION IN PLANTS

FIELD OF THE INVENTION

The present invention relates to compositions and methods for regulating metabolism in plants to control the production of fatty acids. In particular, regulating plant fuel metabolism is achieved by metabolic disruption methods such as inhibiting gluconeogenesis or fatty acid oxidation. The fatty acids generated according to the invention may be useful, for example, in the production of biofuels.

BACKGROUND OF THE INVENTION

Long term energy solutions to global energy challenges increasingly include renewable fuels. Renewable energy sources include electric, solar, wind and biofuels. Only biofuels have the potential to act as feedstock for existing refineries and the resulting biofuel will have similar molecular structure to the refined petroleum products currently used for transportation fuel. Current refineries have the capability for hydrogenation and hydrocracking to further refine the fatty acids into usable transportation fuels. Advanced refining reduces the possibility of gelling in lower temperatures which is a criticism of biofuels. Leading biofuel sources include corn, sugar cane, palm, soy and algae. Algae has the potential to produce impressive increases in gallons/acre of oil production compared to other biofuel sources. Some report yields up to 100 times greater (Tachibana, C. (2009). Algae Biofuels: From pond Scum to Jet Fuel (Oregon, United States, RenewableEnergyWorld.com), pp. 2). Unlike agricultural sources for biofuel which require extensive land allotments that compete with natural forests and habitats and compete with food production imparting upward pressure on world food prices, algae-based biofuel can be grown in areas unfavorable for traditional agriculture.

Renewable energy reduces dependency on limited foreign-controlled petroleum supplies. Biofuels burn cleaner and produce less greenhouse emissions. Additionally, the plants consume CO2 to contribute to the mitigation of global warming.

Many challenges for biofuels remain, including availability and distribution of biofuel pumps, capacity for large scale production, pollution from the extraction processes inherent of biofuels, and current tariff and subsidy policies which benefits only corn-based ethanol.

"Currently about 9 percent of the nation's liquid fuel supply comes from biofuels—most of it corn-based ethanol. And by 2022 Congress has mandated that biofuel levels reach 36 billion gallons." (Mouawad, 2009 Exxon to Invest Millions to Make Fuel From Algae. In NY Times Com (New York, The New York Times).) This renewable fuel standard (RFS) poses a challenge for algae-based fuels as the Federal law does not include algae in its recipe of acceptable biofuels that should make up this 36 billion gallons.

There are several emerging algae-based biofuel companies pursuing commercial biofuel production. Sapphire Energy, based in La Jolla, Calif. recently announced "it would be producing 1 million gallons of diesel and jet fuel a year by 2011, double its initial estimates" (Howell, K. (2009). Is Algae the Biofuel of the Future? In Scientific American (Greenwire).) and that "it will be producing more than 100 million gallons a year by 2018 and 1 billion gallons a year by 2020" (Howell, 2009) almost 3 percent of the RFS. Sapphire is one of the largest and most respected players in the industry with CJ Warner, a 10 year BP oil executive, as CEO and listing Bill Gates and the Rockefeller family as key supporters.

Continental Airlines successfully tested Sapphire Energy's algae-based biodiesel jet fuel in a test flight on Jan. 7, 2009 in a Boeing 737-800 aircraft. Continental reported an increase in mileage attained with the algae-based biofuel due to lower burning temperatures in the engines.

Exxon Energy, a leader in global energy, has partnered with Synthetic Genomics, an algae-based biofuel company led by genomics expert J. Craig Venter. Exxon-Synthetic Genomics utilizes genetically engineered microalgae to continuously secrete oil and potentially simplify the harvesting process by simply skimming the oil from the surface.

SUMMARY OF THE INVENTION

The invention in some aspects relates to the discovery that metabolic disruption, a concept that was originated for the treatment of tumors, especially drug resistant tumors, involving interfering with tumor specific energy pathways, is useful for promoting synthesis and storage of significant quantities of fatty acids. Cells use metabolic processes to meet their energy demands, particularly switching between glucose utilization/oxidation and the oxidation of fatty acids. Importantly, in plants, lipids/fatty acids can be utilized to generate glucose (gluconeogenesis) and can, upon demand, switch from gluconeogenesis to the oxidation of glucose as energy to synthesize and store fatty acids. In sunlight, photosynthetic plants can harvest energy from sunlight depending upon the availability of sunlight. Plants, like mammals, can alternate between meeting their energy demands as a function of fuel availability, internal or external stressors (temperature or water availability, nutrient availability), or fuel demands on to the cell.

The data supporting the invention reveals that organisms, such as *Schizochytrium*, an algae-like, salt water/deep ocean fungus that fish consume, plants including algae, and plant seeds can be manipulated to produce and/or store significant amounts of fatty acids. Each of these organisms express a mitochondrial uncoupling protein that serves at least two functions: (1) a metabolic switch to promote fatty acid oxidation, and (2) a mechanism for preventing, and potentially repairing, free radical and oxidative damage to the organism. Utilizing uncoupling proteins, cells are able to switch from burning glucose to burning fatty acid derived carbons; and from using stores of fatty acids or lipids to using alternate sources of energy (i.e., glucose utilization or sunshine). This "lipid switch" is present in plants when they go dormant for the winter, when there is no available sunlight, or when other energy is unavailable.

In some aspects the invention is a method for preparing a biofuel, by disrupting a fatty acid metabolism pathway in a plant cell or fungus by contacting the plant cell or fungus with an inhibitor of fatty acid metabolism in an effective amount to promote accumulation or storage of fatty acids, collecting the fatty acids from the plant cell or fungus, and processing the fatty acids to produce a biofuel. In one embodiment the fatty acid metabolism pathway is gluconeogenesis. In another embodiment the fatty acid metabolism pathway is fatty acid oxidation.

In some embodiments the inhibitor of fatty acid metabolism is an inhibitor of fatty acid oxidation, a fatty acid transporter inhibitor, a reductase inhibitor, or an isomerase inhibitor within the fatty acid metabolism pathway. The inhibitor of fatty acid metabolism may be an inhibitor of fatty acid oxidation such as an oxirane carboxylic acid compound, such as etomoxir (2-(6-(4-chlorophenoxy)-hexyl)-oxirane-2-carboxylic acid ethyl ester), 2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(5 (4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, 2-(6-phenoxyhexyl)-oxirane-2-carboxylic acid ethyl ester, cerulenin, 5-(tetradecyloxy)-2-furoic acid, oxfenicine, methyl palmoxirate, metoprolol, amiodarone, perhexiline, aminocamitine, hydrazonopropionic acid, 4-bromocrotonic acid, trimetazidine, ranolazine, hypoglycin, dichloroacetate, methylene cyclopropyl acetic acid, beta-hydroxy butyrate, and a non-hydrolyzable analog of camitine or pharmacologically acceptable salts thereof.

In other embodiments the inhibitor of fatty acid metabolism is an inhibitory nucleic acid. The inhibitory nucleic acid may be specific for an enzyme selected from the group consisting of 2,4-dienoyl-CoA reductase, 2,4-dienoyl-CoA isomerase, and butyryl dehydrogenase.

In other embodiments the inhibitor of fatty acid metabolism is a gluconeogenesis inhibitor. The gluconeogenesis inhibitor may be oxamate.

In yet other embodiments the inhibitor of fatty acid metabolism is an inhibitor of UCP. The inhibitor of UCP may be selected from the group consisting of UCP antisense, UCP siRNA, tocopherols and non-omega 3 or 6 fatty acids.

In some embodiments the biofuel is syngas. The syngas may be processed by a Fischer-Tropsch reaction to produce a biodiesel. In other embodiments the biofuel is biodiesel. The biodiesel may be processed using a transesterification process such as that achieved by mixing the fatty acids with methanol. In other embodiments the fatty acids are processed to produce biofuel using a thermochemical liquification process. The fatty acids may also be processed to produce biofuel using a pyrolysis process.

The plant or fungus may be for instance an algae, a plant seed, or a *schizochytrium*.

In some embodiments the disruption of the fatty acid metabolism pathway further comprises contacting the plant cell or fungus with a glycolytic inhibitor. The glycolytic inhibitor may be a 2-deoxyglucose compound.

A method for producing fatty acids, is provided in other aspects of the invention. The method involves disrupting a fatty acid metabolism pathway in a plant cell or fungus by contacting the plant cell or fungus with an inhibitor of fatty acid metabolism in an effective amount to promote accumulation or storage of fatty acids, and collecting the fatty acids, wherein the inhibitor of fatty acid metabolism is not a UCP inhibitor.

In another aspect the invention is a method for producing fatty acids, by disrupting a fatty acid metabolism pathway in a plant cell or fungus by contacting the plant cell or fungus with an inhibitor of fatty acid metabolism in an effective amount to promote accumulation or storage of fatty acids, and collecting the fatty acids as a source of biofuel.

In some embodiments the inhibitor of fatty acid metabolism is an inhibitor of fatty acid oxidation, a fatty acid transporter inhibitor, a reductase inhibitor, or an isomerase inhibitor within the fatty acid metabolism pathway. The inhibitor of fatty acid metabolism may be an inhibitor of fatty acid oxidation such as an oxirane carboxylic acid compound, such as etomoxir (2-(6-(4-chlorophenoxy)-hexyl)-oxirane-2-carboxylic acid ethyl ester), 2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(5 (4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, 2-(6-phenoxyhexyl)-oxirane-2-carboxylic acid ethyl ester, cerulenin, 5-(tetradecyloxy)-2-furoic acid, oxfenicine, methyl palmoxirate, metoprolol, amiodarone, perhexiline, aminocamitine, hydrazonopropionic acid, 4-bromocrotonic acid, trimetazidine, ranolazine, hypoglycin, dichloroacetate, methylene cyclopropyl acetic acid, beta-hydroxy butyrate, and a non-hydrolyzable analog of camitine or pharmacologically acceptable salts thereof.

In other embodiments the inhibitor of fatty acid metabolism is an inhibitory nucleic acid. The inhibitory nucleic acid may be specific for an enzyme selected from the group consisting of 2,4-dienoyl-CoA reductase, 2,4-dienoyl-CoA isomerase, and butyryl dehydrogenase.

In other embodiments the inhibitor of fatty acid metabolism is a gluconeogenesis inhibitor. The gluconeogenesis inhibitor may be oxamate.

In yet other embodiments the inhibitor of fatty acid metabolism is an inhibitor of UCP. The inhibitor of UCP may be selected from the group consisting of UCP antisense, UCP siRNA, tocopherols and non-omega 3 or 6 fatty acids.

In some embodiments the fatty acids are used as a source of biofuel.

A method for producing a syngas, by disrupting a fatty acid metabolism pathway in a plant cell or fungus in an effective amount to promote accumulation or storage of fatty acids, subjecting the plant cell or fungus to a gasification process and collecting syngas produced by the gasification process is provided in other aspects of the invention.

A syngas composed of a gaseous mixture of hydrogen and carbon monoxide produced from a plant cell or fungus in which a fatty acid metabolism pathway has been disrupted is provided in other aspects of the invention.

In another aspect the invention is biodiesel comprising a liquid diesel fuel produced from a plant cell or fungus in which a fatty acid metabolism pathway has been disrupted.

In some aspects the invention is an algae comprising a stably-integrated polynucleotide encoding an RNAi construct, wherein the RNAi construct is complementary to a portion of a target gene, and wherein the target gene participates in fatty acid storage or metabolism.

The polynucleotide encoding the RNAi construct may be, for instance, a plasmid or a retroviral vector or a lentiviral vector. In some embodiments the polynucleotide encoding the RNAi construct is stably integrated into a defined locus of the genome.

In other embodiments a single copy of the polynucleotide encoding the RNAi construct is stably integrated into a defined locus of the genome. For instance, the polynucleotide encoding the RNAi construct may be stably integrated into a defined locus of the genome via Cre-mediated recombination. Alternatively, the polynucleotide encoding the RNAi construct may be stably integrated into a defined locus of the genome via FLP/FRT-mediated recombination.

In some embodiments the RNAi construct is short hairpin RNA (shRNA) or microRNA (miRNA).

Optionally, the algae may further comprise a stably-integrated polynucleotide encoding an Acetyl CoA Carboxylase (ACCase) gene.

In other aspects the invention is a plant cell comprising a stably-integrated polynucleotide encoding an RNAi construct, wherein the RNAi construct is complementary to a portion of a target gene, and wherein the target gene participates in fatty acid storage or metabolism. Optionally the plant cell further comprises a stably-integrated polynucleotide encoding an Acetyl CoA Carboxylase (ACCase) gene.

A method of detecting fat accumulation in an algae is provided in other aspects. The method involves staining an algae with lysosensor and performing a lysosensor detection step to detect fat accumulation in the algae. In some embodiments the detection step is flow cytometry.

Each of the limitations of the invention can encompass various embodiments of the invention. It is, therefore, anticipated that each of the limitations of the invention involving any one element or combinations of elements can be included in each aspect of the invention.

DETAILED DESCRIPTION

Figure 1:
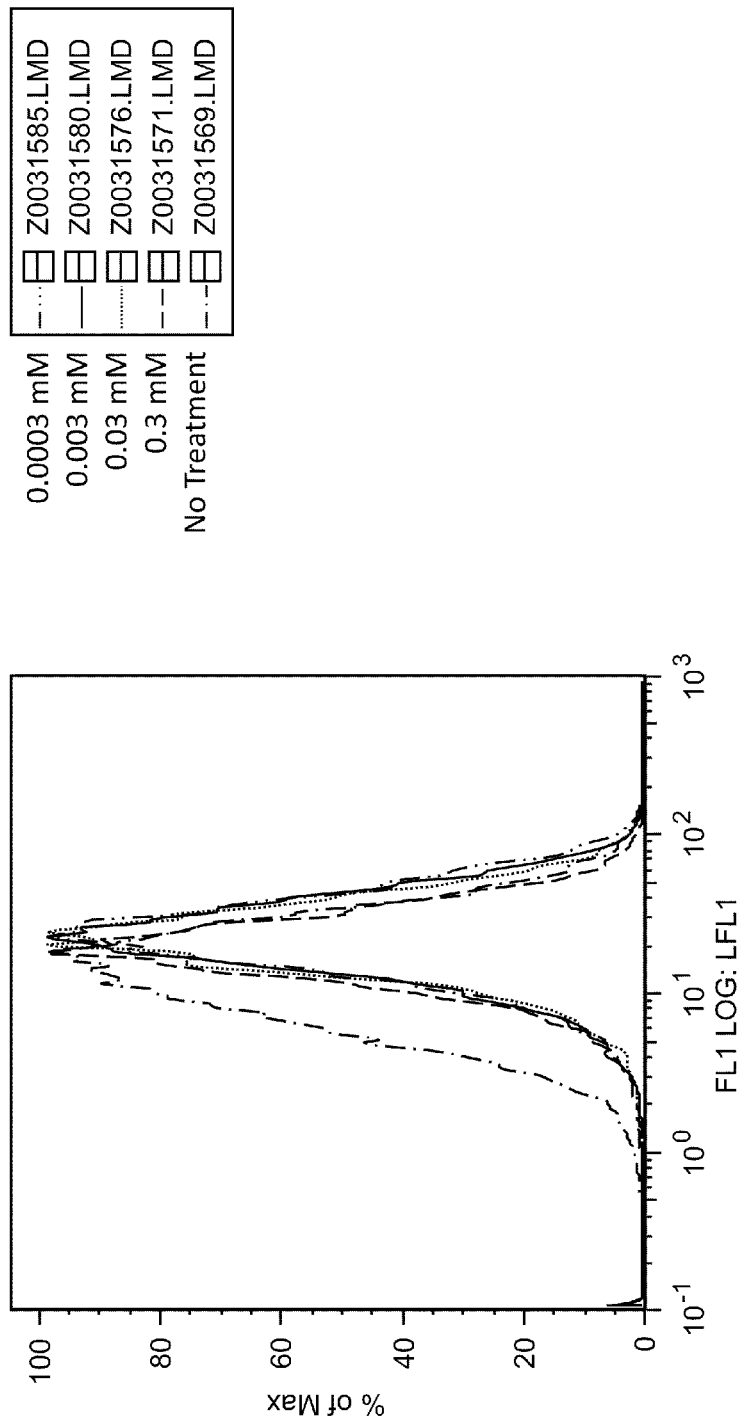
FIG. 1 depicts histograms of *Schizochytrium* either untreated or treated with various concentrations of oxamate. The histograms depict quantities of Lysosensor as a measurement of fatty acid content in oil bodies, glyoxosomes, or lipid laden-organelles. Fl1 is fluorescence resulting from Lysosensor dye. As shown in the Figure, the lowest concentration of oxamate was the most effective at producing high levels of fatty acid accumulation.

Cells require energy to perform the work of maintaining molecular organization, including creating new molecules, reproducing or dividing, moving, dying, or even surviving by become dormant in a hostile environment. The processes required to perform these functions are tightly controlled and regulated through the chemical processes collectively known as metabolism. Energy that is stored in the form of organic molecules, including sugars, lipids, or proteins, becomes available when those molecules are broken down. In contrast, energy is used to synthesize new, and often more complex, molecules from simple ones.

The energy "currency" of the cell is the small molecule adenosine triphosphate (ATP). The generation of ATP requires energy and can occur in at least two ways. The first occurs when sugar (glucose) is broken down in the interior of the cell by a process known as glycolysis. The second occurs through a complex series of events in the mitochondria, known as cellular respiration.

Plants use light energy to produce sugars for use in metabolic work through a process known as photosynthesis. Photosynthetic organisms obtain the energy they need in the form of ATP through photosynthesis, but seeds need an additional source of energy because seeds are not photosynthetic. Seeds store complex molecules, including carbohydrate, oil, and protein, as their energy reserve until conditions allow germination and photosynthesis. As a result, seeds are a rich source of nutrients and a potential reserve for biofuels.

It has been discovered according to the invention that the metabolic processing of fatty acids in plants, including algae (*Chlamydomonas reinhardtii*) and types of fungi which are algae-like (*Schizochytrium*), and seeds, can be disrupted in a manner that results in the accumulation and/or storage of significant amounts of lipids (fatty acids) typically in the form of triacylglycerols (TAGS) which are a preferable form of natural oil for conversion to biofuels. These organisms express uncoupling proteins that appear to be required for fatty acid oxidation, which once inhibited, results in storage and secretion of fatty acids. Thus, metabolic modifiers, including inhibitors such as small molecule and nucleic acid inhibitors as well as activators of specific metabolic processes, can increase the stored energy reserves in a broad spectrum of organisms, thereby increasing their use as biofuels.

Prior to the invention a study examined an enzyme involved in catalyzing a key metabolic step in the synthesis of oils in algae. This study is described in Sheehan et al (The US Department of Energy's Aquatic Species Program: Biodiesel from Algae (1998). A Look Back at the US Department of Energy's Aquatic Species Program—Biodiesel from Algae, U. D. o. E. s. O. o. F. Development, ed. (Golden, Colo., National Renewable Energy Laboratory)). Sheehan et al suggests that the discovery of this enzyme, referred to as Acetyl CoA Carboxylase (ACCase) led to hope that expression of the enzyme in algae would result in higher production levels of fatty acids for use as a biofuel. Although this enzyme was necessary for the metabolic process of oil production in algae, forced expression of the ACCase gene did not demonstrate increased oil production in the cells.

In contrast to this finding, Applicants have demonstrated that disrupting or inhibiting fatty acid metabolism in plant and fungal cells results in significantly increased oil production in these cells. Thus, in some aspects the invention relates to methods for promoting increased accumulation or storage of fatty acids in plants or fungi. Increased accumulation or storage refers to any increase with respect to a plant cell or fungus that has not been treated or altered according to the methods of the invention. The amount of fatty acids stored within a cell can be assessed by any methodology known in the art. For example methods for measuring fatty acid accumulation in a cell are described in the Examples section and include flow cytometry.

The methods described herein are useful in plant cells or fungi. As used herein, the term "plant" is used in its broadest sense. The term plant includes, but is not limited to, any species of woody, ornamental or decorative, crop or cereal, fruit or vegetable plant, and algae (e.g., *Chlamydomonas reinhardtii*). As used herein, the term "cereal crop" is used in its broadest sense. The term includes, but is not limited to, any species of grass, or grain plant (e.g., barley, corn, oats, rice, wild rice, rye, wheat, millet, sorghum, triticale, etc.), non-grass plants (e.g., buckwheat flax, legumes [soybeans] etc.). As used herein, the term "crop" or "crop plant" is used in its broadest sense. The term includes, but is not limited to, any species of plant or algae edible by humans or used as a feed for animals or used, or consumed by humans, or any plant or algae used in industry or commerce. As used herein, the term "dark-dier" refers to a class of mutant organisms strains that are obligate phototrophs, including but not limited to, mutant strains of *Chamydomonas reinhardtii*.

Algae, alga or the like, refer to plants belonging to the subphylum Algae of the phylum Thallophyta. There are over 40,000 wild algal species, but most leading companies genetically engineer or select the strains for oil production. Photosynthesizing algae require only photosynthesis, $CO_2$ and water which the plant uses to produce glucose and further metabolizes into lipids or oil as stored fuel for an uncertain future. The algae are unicellular, photosynthetic, and are non-parasitic plants without roots, stems or leaves. They contain chlorophyll and have a great variety of sizes, from microscopic to large seaweeds. Green algae, including Eukaryota, Viridiplantae, Chlorophyta, Chlorophyceae, are particularly useful in the invention. *C. reinhardtii* is a Volvocales—Chlamydomonadaceae. However, algae useful in the invention may also be blue-green, red, or brown, so long as the algae is able to produce fatty acids.

*Chlamydomonas* is a genus of unicellular green algae (Chlorophyta) that is found all over the world. More than 500 different species of *Chlamydomonas* are known, but the most widely used laboratory species is *Chlamydomonas reinhardtii*. *C. reinhardtii*, is a unicellular green algae that has been a useful model for many types of studies, including photosynthesis and motility. Photosynthesis, when light is available, and acetate when light is not, are involved in energy production and consumption in *C. reinhardtii*.

The most common oil-producing algae can generally include, or consist essentially of, the diatoms (bacillariophytes), green algae (chlorophytes), blue-green algae (cyanophytes), and golden-brown algae (chrysophytes). In addition a fifth group known as haptophytes may be used. Specific non-limiting examples of bacillariophytes capable of oil production include the genera *Amphipleura, Amphora, Chaetoceros, Cyclotella, Cymbella, Fragilaria, Hantzschia, Navicula, Nitzschia, Phaeodactylum*, and *Thalassiosira*. Specific non-limiting examples of chlorophytes capable of oil production include *Ankistrodesmus, Botryococcus, Chlorella, Chlorococcum, Dunaliella, Monoraphidium, Oocystis, Scenedesmus*, and *Tetraselmis*. In one aspect, the chlorophytes can be *Chlorella* or *Dunaliella*. Specific non-limiting examples of cyanophytes capable of oil production include *Oscillatoria* and *Synechococcus*. A specific example of chrysophytes capable of oil production includes *Boekelovia*. Specific non-limiting examples of haptophytes include *Isochysis* and *Pleurochysis*. In one aspect, the oil-producing algae or plant cells can have oil content greater than about 20%, and preferably greater than about 30% or 40% or 50% by weight of the algae.

An oil-producing algae can be cultivated in a cultivation sub-system. Both autotrophic and heterotrophic growth can be used to produce a useful quantity of algae and for the algae to produce useful oil. The autotrophic growth and heterotrophic growth can also be sequentially performed in a multiple stage process. The algae can be grown in a greenhouse environment such as the raceway ponds as described above, although other growth environments may also be suitable. Non-limiting examples of growth environments or reservoirs which can be used include bioreactors, open ponds having various shapes and configurations.

Fungi, as used herein, refer to fungi capable of photosynthesis. An example of a photosynthesizing fungi is *Schizochytrium*, an algae-like, salt water/deep ocean fungus that fish consume. Fungus also include yeast and other autotrophic organisms.

Yeast are single celled fungi. Classification for yeast involves the characteristics of the cell, ascospore, colony, and physiological characteristics all of which are used to identify a particular species of yeast. A well-known characteristics is the ability to ferment sugars for the production of ethanol. Budding yeasts are fungi from Ascomycetes class; Saccharomycetes (also called Hemiascomycetes). The true yeasts are separated into one main order Saccharomycetales. The most well-known and commercially significant yeasts are the related species and strains of *Saccharomyces cerevisiae*.

Free energy consumed by biological systems originates as solar energy. Photosynthetic organisms have evolved the processes of photosynthesis to take advantage of the solar radiation reaching the earth. Essentially, photosynthesis is a light-induced redox process in which carbon dioxide is reduced to a metabolizable storage compound by an external reductant (i.e., light is used to create reducing potential). Photosynthetic organisms are primarily classified by the nature of the reductant used during photosynthetic processes. Oxygenic photosynthetic organisms, for instance, are distinguished from prokaryotic photosynthetic organisms primarily by their ability to use water as a reductant. Plants, algae, cyanobacteria, and prochlorophytes are all oxygenic photosynthetic organisms. Green plants photosynthesis takes place in chloroplasts. The systems that convert solar energy in green plants to useful metabolic energy are integrated into the thylakoid membrane system of green plant chloroplasts. In particular, the thylakoid membranes contain the energy-transducing machinery: the light-harvesting-proteins, reaction centers, electron transport chains, and ATP synthase. Photosynthesis in green plants begins by the absorption of light by a chlorophyll porphyrin (i.e., with a coordinated magnesium ion). The resulting electronic excitation passes along a series of chlorophyll molecules until the excitation is trapped in a reaction center. In the reaction center the energy of light (i.e., electron excitation) is converted into a separation of charge (i.e., reducing potential). Green plants use two light reactions: photosystem I and photo system II. Photosystem I generates reducing potential in the form of NADPH. Photosystem II transfers the electrons of water to a quinone and concomitantly evolves diatomic oxygen. The flow of electrons in, and between, both photosystem generates a proton gradient across the thylakoid membrane that drives the synthesis of ATP. The ATP and NADPH that results from photophosphorylation processes in green plants are used to reduce carbon dioxide and convert it into 3-phosphoglycerate. The electron-motive force generated in green plant chloroplast photosystems drives electron transfer in a opposite direction from that in mitochondria. In photosynthesis, electrons are taken from water to produce diatomic oxygen, and concomitantly used to reduce carbon dioxide to synthesize carbohydrates. Chloroplasts, therefore, generate diatomic oxygen and carbohydrate, while mitochondria consume oxygen and carbohydrate.

The fungi or plant cells may be cultured in natural or artificial environments. The use of the word "culture" is meant to refer to the propagation of living cells in media that is conducive to growth under the appropriate environmental conditions. Thus, culture includes natural environments for plants and fungi. The most common non-natural or cultured media include broths, gelatin, and agar. The culture may be solid or liquid. Culturing may be done on a commercial scale, or in a single Petri dish.

The methods of the invention involve disrupting a fatty acid metabolism pathway in a plant cell or fungus by contacting the plant cell or fungus with an inhibitor of fatty acid metabolism in an effective amount to promote accumulation or storage of fatty acids. The term "disrupting a fatty acid metabolism pathway" as used herein refers to any interruption in the processing of cellular fatty acids. An interruption in the processing of cellular fatty acids leads to increased accumulation or storage of such fatty acids. A fatty acid metabolism pathway is defined as including pathways such as gluconeogenesis (conversion of fatty acids into sugars/carbohydrates), fatty acid oxidation (conversion of fatty acids into energy) and uncoupling protein (UCP).

Metabolic disruption of fatty acids can be achieved using inhibitors of fatty acid metabolism. A "fatty acid metabolism inhibitor," as used herein, is a compound able to inhibit (e.g., prevent, or at least decrease or inhibit the activity by an order of magnitude or more) a reaction within the fatty acid metabolism pathway, such as an enzyme-catalyzed reaction within the pathway. The inhibitor may inhibit the enzyme, e.g., by binding to the enzyme or otherwise interfering with operation of the enzyme (for example, by blocking an active site or a docking site, altering the configuration of the enzyme, competing with an enzyme substrate for the active site of an enzyme, etc.), and/or by reacting with a coenzyme, cofactor, etc. necessary for the enzyme to react with a substrate. The fatty acid metabolism pathway is the pathway by which fatty acids are metabolized within a cell for energy (e.g., through the synthesis of ATP and the breakdown of fatty acids into simpler structures, such as $CO_2$, acyl groups, etc.) or to produce a carbohydrate source. For example inhibitors of fatty acid metabolism include inhibitors of gluconeogenesis, inhibitors of fatty acid oxidation, fatty acid transporter inhibitors, reductase inhibitors, isomerase inhibitors within the fatty acid metabolism pathway, and inhibitors of UCP.

An inhibitor of gluconeogenesis is a compound that prevents at least some and preferably a substantial amount of fatty acid conversion into carbohydrates such as glucose. For example, glycolytic inhibitors, oxamate and iodoacetate are inhibitors of gluconeogenesis. Oxamate, as shown in the Examples, has been demonstrated to be a potent inhibitor of gluconeogenesis that causes increased accumulation or storage of fatty acids in plant cells and fungi. A glycolytic inhibitor may also be used in the methods of the invention. Preferred glycolytic inhibitors are 2-deoxyglucose compounds, defined herein as homologs, analogs, and/or derivatives of 2-deoxy-D-glucose. Glycolytic inhibitors particularly useful herein can have the formula:

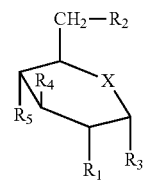

wherein: X represents an O or S atom; $R_1$ represents a hydrogen atom or a halogen atom; $R_2$ represents a hydroxyl group, a halogen atom, a thiol group, or CO—$R_6$; and $R_3$, $R_4$, and $R_5$ each represent a hydroxyl group, a halogen atom, or CO—$R_6$ wherein $R_6$ represents an alkyl group of from 1 to 20 carbon atoms, and wherein at least two of R3, R4, and Rs are hydroxyl groups. The halogen atom is as described above with respect to the oxirane carboxylic acid compounds, and in $R_2$, $R_3$, $R_4$, and $R_5$. The halogen atom is preferably F, and $R_6$ is preferably a $C_3$-$C_{15}$ alkyl group. A preferred glycolytic inhibitor is 2-deoxy-D-glucose The fatty acid metabolism pathway includes several enzymatic reactions, which use various enzymes such as reductases or isomerases. Specific examples of enzymes within the fatty acid metabolism pathway include 2,4-dienoyl-CoA reductase, 2,4-dienoyl-CoA isomerase, butyryl dehydrogenase, etc, as further discussed below. In one embodiment, the fatty acid metabolism inhibitor is an inhibitor able to inhibit a beta-oxidation reaction in the fatty acid metabolism pathway. In another embodiment, the inhibitor is an inhibitor for a fatty acid transporter (e.g., a transporter that transports fatty acids into the cell, or from the cytoplasm into the mitochondria for metabolism). In yet another embodiment, the inhibitor may react or otherwise inhibit key steps within the fatty acid metabolism pathway. In still another embodiment, the inhibitor may be an inhibitor of fatty acids as a source of energy in the mitochondria. For example, the inhibitor may inhibit the breakdown of intermediates such as butyryl CoA, glutaryl CoA, or isovaleryl CoA.

2,4-dienoyl-CoA reductase is an enzyme within the fatty acid metabolism pathway that catalyzes reduction reactions involved in the metabolism of polyunsaturated fatty acids. Certain fatty acids are substrates for 2,4-dienoyl-CoA reductases located within the mitochondria. In some cases, fatty acids may be transported into the mitochondria through uncoupling proteins. The uncoupling protein may, in certain instances, increase the mitochondrial metabolism to increase the availability of fatty acids within the mitochondria and/or increase the throughput of beta-oxidation within the mitochondria.

The enzyme 2,4-dienoyl-CoA isomerase is an enzyme within the fatty acid metabolism pathway that catalyzes isomerization of certain fatty acids. One step in the metabolism of certain polyunsaturated fatty acids may be protective against reactive oxygen intermediates ("ROI"). Thus, by generating substrates and antagonists for the activity of 2,4-dienyol-CoA isomerase, the metabolic production of reactive oxygen intermediates may be enhanced and/or reduced. This, in turn, affects the levels of fatty acids in the cell.

Thus, it is to be understood that, as used herein, compounds useful for inhibiting fatty acid metabolism (i.e., "fatty acid metabolism inhibitors") are also useful for altering cellular production of reactive oxygen; compounds described in reference to fatty acid metabolism inhibition should also be understood herein to be able to alter reactive oxygen production within a cell. For example, by altering the ability of a cell to metabolize a fatty acid, the ability of the cell to produce reactive oxygen may also be affected, since one pathway for a cell to produce reactive oxygen intermediates is through the metabolism of fatty acids. Thus, in some cases, the production of reactive oxygen can be affected by exposing a cell to, or removing a cell from, a fatty acid metabolism inhibitor.

In a preferred embodiment of the invention, the fatty acid inhibitor is an oxirane carboxylic acid compound. In accordance with a discovery of this invention, such compounds, exemplified by etomoxir, are able to alter cellular production of reactive oxygen. Preferred oxirane carboxylic acid compounds have the formula:

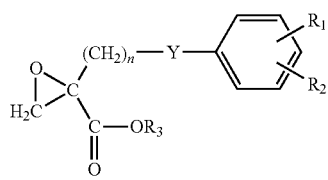

wherein: $R_1$ represents a hydrogen atom, a halogen atom, a 1-4C alkyl group, a 1-4C alkoxy group, a nitro group or a trifluoromethyl group; $R_2$ has one of the meanings of $R_1$; $R_3$ represents a hydrogen atom or a 1-4C alkyl group; Y represents the grouping —O—$(CH_2)$m-; m is 0 or a whole number from 1 to 4; and n is a whole number from 2 to 8 wherein the sum of in and n is a whole number from 2 to 8. More preferred are oxirane carboxylic acid compounds wherein $R_1$ is a halogen atom, $R_2$ is a hydrogen atom, m is 0, and n is 6, and more particularly where $R_3$ is an ethyl group.

It is most particularly preferred to use etomoxir, i.e., 2-(6-(4-chlorophenoxy)-hexyl)-oxirane-2-carboxylic acid ethyl ester. Examples of other oxirane carboxylic acid compounds useful in the invention are 2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(5 (4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, and 2-(6-phenoxyhexyl)-oxirane-2-carboxylic acid ethyl ester, the corresponding oxirane carboxylic acids, and their pharmacologically acceptable salts.

The foregoing class of oxirane carboxylic acid compounds, including etomoxir, has been described by Horst Wolf and Klaus Eistetter in U.S. Pat. No. 4,946,866 for the prevention and treatment of illnesses associated with increased cholesterol and/or triglyceride concentration, and by Horst Wolf in U.S. Pat. No. 5,739,159 for treating heart insufficiency. The preparation of oxirane carboxylic acid compounds, and their use for blood glucose lowering effects as an ant diabetic agent, is described in Jew et al U.S. Pat. No. 6,013,666. Etomoxir has been described as an inhibitor of mitochondrial carnitine palmitoyl transferase-I by Mannaerts, G. P., L. J. Debeer, J. Thomas, and P. J. De Schepper "Mitochondrial and peroxisomal fatty acid oxidation in liver homogenates and isolated hepatocytes from control and clofibrate-treated rats," J. Biol. Chem. 254:4585-4595, 1979.

The foregoing U.S. Pat. Nos. 4,946,866, 5,739,159, and 6,013,666, United States Patent Application 20030036199, and the foregoing publication by Mannaerts, G. P., L. J. Debeer, J. Thomas, and P. J. De Schepper, are incorporated herein by reference. In addition, U.S. patent application Ser. No. 10/272,432, filed Oct. 15, 2002, entitled "Methods for Regulating Co-Stimulatory Molecule Expression with Reactive Oxygen," by M. K. Newell, et al. is incorporated herein by reference in its entirety.

Other, non-limiting examples of fatty acid metabolism inhibitors include fatty acid transporter inhibitors, beta-oxidation process inhibitors, reductase inhibitors, and/or isomerase inhibitors within the fatty acid metabolism pathway. Specific examples of other fatty acid metabolism inhibitors include, but are not limited to, cerulenin, 5-(tetradecyloxy)-2-furoic acid, oxfenicine, methyl palmoxirate, metoprolol, amiodarone, perhexiline, aminocamitine, hydrazonopropionic acid, 4-bromocrotonic acid, trimetazidine, ranolazine, hypoglycin, dichloroacetate, methylene cyclopropyl acetic acid, and beta-hydroxy butyrate. Structural formulas for these inhibitors are shown in FIGS. 1A-1C. As a another example, the inhibitor may be a non-hydrolyzable analog of carnitine.

In one embodiment, the fatty acid metabolism inhibitor is a carboxylic acid. In some cases, the carboxylic acid may have the structure:

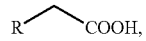

where R comprises an organic moiety, as further described below. In some cases, R may include at least two nitrogen atoms, or R may include an aromatic moiety (as further described below), such as a benzene ring, a furan, etc.

In another embodiment, the fatty acid metabolism inhibitor has the structure:

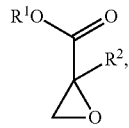

where each of $R^1$ and $R^2$ independently comprises organic moiety. In some instances, either or both of $R^1$ and $R^2$ may independently be an alkyl, such as a straight-chain alkyl, for instance, methyl, ethyl, propyl, etc. In certain cases, $R^2$ may have at least 5 carbon atoms, at least 10 carbon atoms, or at least 15 or more carbon atoms. For example, in one embodiment, $R^2$ may be a tetradecyl moiety. In other cases, $R^2$ may include an aromatic moiety, for example, a benzene ring. In still other cases, $R^2$ may have the structure:

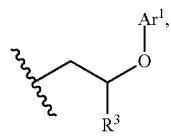

where $R^3$ comprises an organic moiety and $Ar^1$ comprises an aromatic moiety. $R^3$ may be a an alkyl, such as a straight-chain alkyl. In some instances, $Ar^1$ may be a benzene ring or a derivative thereof, i.e., having the structure:

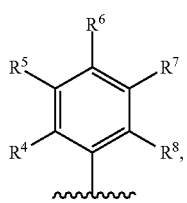

wherein each of $R^4$, $R^5$, $R^6$, $R^7$, and $R^8$ is hydrogen, a halogen, an alkyl, an alkoxy, etc.

In yet another embodiment, the fatty acid metabolism inhibitor has the structure:

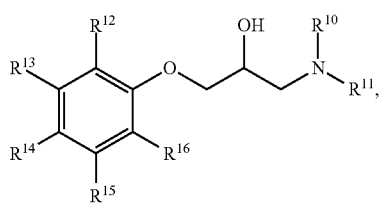

where each of $R^{10}$, $R^{11}$, $R^{12}$, $R^{13}$, $R^{14}$, $R^{15}$ and $R^{16}$ independently comprises hydrogen, a halogen, or an organic moiety, such as an alkyl, an alkoxy, etc. In some cases, $R^{10}$ and $R^{11}$ together may define an organic moiety, such as a cyclic group. For example, the fatty acid metabolism inhibitor may have the structure:

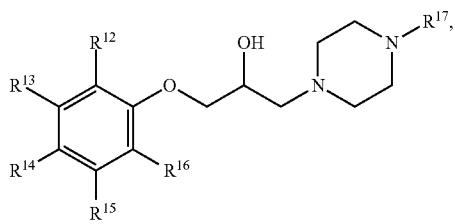

wherein $R^{17}$ comprises an organic moiety, such as an alkyl, an alkoxy, an aromatic moiety, an amide, etc. An example of $R^{17}$ is:

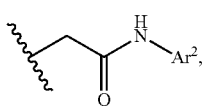

wherein $Ar^2$ comprises an aromatic moiety, such as a benzene ring or a benzene derivative, as previously described.

In still another embodiment, the fatty acid metabolism inhibitor includes a dominant negative plasma membrane polypeptide. The end result of the use (e.g., expression) of a dominant negative polypeptide in a cell may be a reduction in functional enzymes present within the fatty acid metabolism pathway. One of ordinary skill in the art can assess the potential for a dominant negative variant of a protein or enzyme, and use standard mutagenesis techniques to create one or more dominant negative variant polypeptides. For example, one of ordinary skill in the art can modify the sequence of an enzyme coding region by site-specific mutagenesis, scanning mutagenesis, partial gene deletion or truncation, and the like. See, e.g., U.S. Pat. No. 5,580,723 and Sambrook, et al., *Molecular Cloning: A Laboratory Manual*, Second Edition, Cold Spring Harbor Laboratory Press, 1989. One of ordinary skill in the art then can test the population of mutagenized polypeptides for diminution in a selected and/or for retention of such activity of the protein or enzyme. Other similar methods for creating and testing dominant negative variants of a protein will be apparent to one of ordinary skill in the art.

In another set of embodiments, the cells may be exposed to an agent that inhibits the synthesis or production of one or more enzymes within the fatty acid metabolism pathway. Exposure of the cells to the agent thus inhibits fatty acid metabolism within the cell. For example, in one embodiment, an antisense oligonucleotide may be used that selectively binds to regions encoding enzymes present within the fatty acid metabolism pathway, such as 2,4-dienoyl-CoA reductase or 2,4-dienoyl-CoA isomerase. Antisense oligonucleotides are discussed in more detail below.

The inhibitor of fatty acid metabolism may also be an inhibitor of UCP. As taught in U.S. Pat. No. 7,105,718 UCP is present in plant cellular membranes other than the mitochondrial membrane. For instance, UCP is expressed on the cell wall, plasma membrane and chloroplasts of light and cold sensitive cells but not of light and cold resistant cells. It is taught therein that inhibitors of UCP are useful for increasing the production of fatty acids in plant cells.

A variety of uncoupling proteins (UCPs) are known to exist in vertebrate and photosynthetic organisms. These proteins are named for the ability to dissipate the above described proton gradient generated by the respective electron transport chains in mammalian mitochondria and green plan chloroplasts. Thus, these proteins are said to uncouple the flow of protons across a membrane through ATP synthetase and prevent the concomitant production of ATP. Dissipation of the proton gradient in this manner produces heat in a process called thermogenesis.

UCP-like proteins occur in each of the four eukaryotic kingdoms: animals, plants, fungi, and protists (See e.g., Jarmuszkiewicz et al., FEBS Lett., 467:145 [2000].) UCPs are encoded by small multi-gene families in both mammals and plants. In mammals, UCP1 is exclusively expressed in brown adipocyte tissue, while UCP2 is expressed in most tissues of humans and rodents (See e.g., Boss et al., Eur. J. of Endorinol. 139, 1-9 [1998]); UCP3 is expressed in both skeletal muscle and in human brown adipoctye tissue (See e.g., Vidal-Puig et al., Biochem. Biophys. Res. Com 235:79 [1997]); and UCP4 is expressed in brain tissues. In mammals, UCP causes a change from glucose to fatty acid oxidation in mitochondria, and consequent thermogenesis in brown adipocyte tissue.

Plant UCP was first identified in potato tuber and has been isolated in *Arabidopsis*. These potato UCP are located in the mitochondria and have been implicated in chill resistance in plants (See e.g., Nantes et al., FEBS Lett., 457:103 [1999].

It was discovered according to the invention that UCP is expressed on other cellular membranes including the plant cell wall, plasma membrane, and the chloroplasts. It was further discovered that the expression and activity of UCP in each of these distinct locations has an important impact on the regulation of cellular metabolism and free radical accumulation. These findings of the invention have important implications in the treatment of disease and the control of cellular metabolism, because it was not previously recognized that UCP was expressed in membranes such as the cell wall and that such expression of UCP was involved in regulating various cellular functions.

The present invention, while not intended to be limited by the selection of a particular uncoupling protein sequences, provides a variety of UCP gene or mRNA sequences, including, but not limited to, 1) plant UCPs: Genbank accession AJ002586 (*Solanum tuberosum* "potato," SEQ ID NO:7), AJ223983 (*Arabidopsis thaliana*, SEQ ID NO:8), AB021706 (*Arabidopsis thaliana*, SEQ ID NO:9), AB024733 (*Symplocarpus renifoliu* "skunk cabbage"); 2) human UCPs: U28480 (UCP), AF096289 (UCP2), AF019409 (UCP2), U7637 (UCP2), AF011449 (UCP3), AF001787 (UCP3), U08476367 (UCP3), AF1104532 (UCP4); 3) mouse UCPs: AAB17666 (UCP), U63418 (UCP), U63419 (UCP), AF096288 (UCP2), AB012159 (UCP2), U69135 (UCP2), AF032902 (UCP3), AF053352 (UCP3), AF030164 (UCP3), AB010742 (UCP3); 4) rat UCPs: NM012682 (UCP), X03894 (UCP), X12925 (UCP), M11814 (UCP), AF039033 (UCP2), AB010743 (UCP2), AB005143 (UCP2), AB006613 (UCP2), AF030163 (UCP3), AB008216 (UCP3), AF035943 (UCP3), AB006614 (UCP3), U92069 (UCP3); 5) pig UCPs: AF111998 (UCP2), 111999 (UCP2), AF036757 (UCP2), A128837 (UCP3), AF095744 (UCP3); 6) cow UCPs: AF092048 (UCP3); 7) dog UCPs: AB020887 (UCP2), AB022020 (UCP3); and 8) rabbit UCP X14696.

The UCP activity may be modified with the use of UCP inhibitors. "UCP activity" refers to an induction of expression of new or exogenous UCP, modulation of the activity of existing UCP, or the translocation of existing sources of UCP to different membranes.

UCP inhibitors are any compounds which decrease the activity of UCP in the cell. UCP inhibitors include but are not limited to UCP binding peptides such as anti-UCP antibodies, UCP anti-sense nucleic acids, UCP RNAi, UCP dominant negative nucleic acids, nucleotides, nucleotide analogs, tocopherols, such as tocotrienols, and non omega 3 or 6 fatty acids. Other types of inhibitors include ribozymes which interfere with the transcription, processing, or translation of UCP mRNA. In other embodiments the UCP inhibitor is tunicamycin. Tunicamycin promotes intracellular trafficking of the UCP between intracellular locations. Each of these inhibitors is well known in the art and has been described extensively in the literature.

Nucleotides and nucleotide (purine and pyrimidine) analogs include but are not limited to guanosine diphosphate (GDP). Purine analogs include but are not limited to guanosine diphosphate, 8-oxo-Adenosine, 8-oxo-Guanosine, 8-fluoro-Adenosine, 8-fluoro-Guanosine, 8-methoxy-Adenosine, 8-methoxy-Guanosine, 8-aza-Adenosine and 8-aza-Guanosine, azacitidine, Fludarabine phosphate, 6-MP, 6-TG, azathiprine, allopurinol, acyclovir, gancylovir, deoxycoformycin, and arabinosyladienine (ara-A), guanosine diphosphate fucose, guanosine diphosphate-2-fluorofucose, guanosine diphosphate-.beta.L-2-aminofucose, guanosine diphosphate-D-arabinose and 2-aminoadenosine. Some examples of pyrimidine analogues are uracil, thymine, cytosine, 5-fluorouracil, 5-chlorouracil, 5-bromouracil, dihydrouracil, 5-methylcytosine, 5-propynylthymine, 5-propynyluracil and 5-propynylcytosine, 5-fluorocytosine, Floxuridine, uridine, thymine, 3'-azido-3'-deoxythymidine, 2-fluorodeoxycytidine, 3-fluoro-3'-deoxythymidine; 3'-dideoxycytidin-2'-ene; and 3'-deoxy-3'-deoxythymidin-2'-ene, cytosine arabinoside. Other such compounds are known to those of skill in the art.

Thus nucleotides and nucleotide analogs can be modified to produce cell wall/plasma membrane targeted UCP inhibitors if so desired by attaching a cell wall/plasma membrane targeting sequence to the nucleotide or nucleotide analog. This can be accomplished by linking the nucleotide analog to a cell surface targeting molecule. Several methods for linking molecules are described below and others are known in the art. The nucleotide or nucleotide analogs may also be optionally modified such that it is membrane impermeable to prevent uptake of the nucleotide analog by the cell. By using compounds which are not taken up by a cell but simply act on the cell surface UCP many of the toxic side effects associated with some of these drugs are avoided.

UCP inhibitors also include UCP binding peptides or molecules. The binding peptides or molecules can be delivered directly to the cell to act on the UCP. The UCP binding peptides and molecules of the invention can be identified using routine assays, such as the binding and activation assays described in the Examples and elsewhere throughout this patent application.

The UCP binding molecules may be isolated from natural sources or synthesized or produced by recombinant means. Methods for preparing or identifying molecules which bind to a particular target are well-known in the art. Molecular imprinting, for instance, may be used for the de novo construction of macro molecular structures, such as peptides, which bind to a particular molecule. See for example, Kenneth J. Shea, *Molecular Imprinting of Synthetic Network Polymers: The De novo Synthesis of Molecular Binding In Catalytic Sites*, Trip, to May 1994; Klaus, Mosbach, Molecular Imprinting, Trends in *Biochem. Sci.*, 19 (9), January 1994; and Wulff, G., In Polymeric Reagents and Catalysts (Ford, W. T., ed.) *ACS Symposium Series* No. 308, P. 186-230, Am. Chem. Soc. 1986. Binding peptides, such as antibodies, may easily be prepared by generating antibodies to UCP (or obtained from commercial sources) or by screening libraries to identify peptides or other compounds which bind to the UCP.

Many UCP antibodies are commercially available. These include but are not limited to those antibodies commercially available from Santa Cruz Biotechnology, Inc., e.g., UCP1 (m-17, sc-6529), UCP1 (C-17, sc-6528), UCP2 (A19, sc-6527), UCP2 (N19, sc-6526), UCP2 (c-20, sc-6525), and UCP3 (C-20, sc-7756); antibodies commercially available from Research Diagnostics Inc e.g., Goat anti-UCP1 HUMAN/Mouse/Rat (cat#RDI-UCP1Cabg); Goat anti-UCP1 HUMAN/Mouse/Rat (cat#RDI-MUCP1Cabg); Goat anti-UCP2 HUMAN/Mouse/Rat (cat#RDI-UCP2Nabg); Goat anti-UCP2 HUMAN/Mouse/Rat (cat#RDI-UCP2Cabg); Goat anti-UCP2 HUMAN/Mouse/Rat (cat#RDI-UCP2C1abg); Rabbit anti-Murine UCP1 (cat#RDI-MUCP12abrX); Rabbit anti-Murine UCP1 (cat#RDI-MUCP19abrX); Rabbit anti-Murine UCP2 (cat#RDI-MUCP2abrX); Rabbit anti-Murine UCP2 (cat#RDI-MUCP2CabrX); Rabbit anti-human UCP2 (cat#RDI-UCP2MabrX); UCP3L (see Boss, O et al (1997) FEBS Lett 408, 38-42; Vidal-Plug A et al (1997) BBRC 235, 79-82); Rabbit anti-HUMAN UCP3 (cat#RDI-UCP3abrX); Rabbit anti-HUMAN UCP3 (cat#RDI-UCP3CbrX); Rabbit anti-HUMAN UCP3 (cat#RDI-UCP3MabrX); Rabbit anti-Rat UCP3 (cat#RDI-RTUCP3MabrX), etc.

Mimics of known binding molecules may also be prepared by known methods, such as (i) polymerization of functional monomers around a known binding molecule or the binding region of an antibody which also binds to the target (the template) that exhibits the desired activity; (ii) removal of the template molecule; and then (iii) polymerization of a second class of monomers in the void left by the template, to provide a new molecule which exhibits one or more desired properties which are similar to that of the template. The method is useful for preparing peptides, and other binding molecules which have the same function as binding peptides, such as polysaccharides, nucleotides, nucleoproteins, lipoproteins, carbohydrates, glycoproteins, steroids, lipids and other biologically-active material can also be prepared. Thus a template, such as a UCP binding antibody can be used to identify UCP inhibitors. It is now routine to produce large numbers of inhibitors based on one or a few peptide sequences or sequence motifs. (See, e.g., Bromme, et al., *Biochem. J.* 315:85-89 (1996); Palmer, et al., *J. Med. Chem.* 38:3193-3196 (1995)). For example, if UCP is known to interact with protein X at position Y, an inhibitor of UCP may be chosen or designed as a polypeptide or modified polypeptide having the same sequence as protein X, or structural similarity to the sequence of protein X, in the region adjacent to position Y. In fact, the region adjacent to the cleavage site Y spanning residues removed by 10 residues or, more preferably 5 residues, N-terminal and C-terminal of position Y, may be defined as a "preferred protein X site" for the choice or design of UCP inhibitors. Thus, a plurality of UCP inhibitors chosen or designed to span the preferred protein X binding site around position Y, may be produced, tested for inhibitory activity, and sequentially modified to optimize or alter activity, stability, and/or specificity.

Binding molecules may also be identified by conventional screening methods, such as phage display procedures (e.g. methods described in Hart et al., *J. Biol. Chem.* 269:12468 (1994)). Hart et al. report a filamentous phage display library for identifying novel peptide ligands. In general, phage display libraries using, e.g., M13 or fd phage, are prepared using conventional procedures such as those described in the foregoing reference. The libraries generally display inserts containing from 4 to 80 amino acid residues. The inserts optionally represent a completely degenerate or biased array of peptides. Ligands having the appropriate binding properties are obtained by selecting those phage which express on their surface a ligand that binds to the target molecule. These phage are then subjected to several cycles of reselection to identify the peptide ligand expressing phage that have the most useful binding characteristics. Typically, phage that exhibit the best binding characteristics (e.g., highest affinity) are further characterized by nucleic acid analysis to identify the particular amino acid sequences of the peptide expressed on the phage surface in the optimum length of the express peptide to achieve optimum binding.

Alternatively, UCP binding molecules can be identified from combinatorial libraries. Many types of combinatorial libraries have been described. For instance, U.S. Pat. Nos. 5,712,171 (which describes methods for constructing arrays of synthetic molecular constructs by forming a plurality of molecular constructs having the scaffold backbone of the chemical molecule and modifying at least one location on the molecule in a logically-ordered array); 5,962,412 (which describes methods for making polymers having specific physiochemical properties); and 5,962,736 (which describes specific arrayed compounds).

To determine whether a molecule binds to the appropriate target any known binding assay may be employed. For example, in the case of a peptide that binds to the UCP the molecule may be immobilized on a surface and then contacted with a labeled UCP (or vice versa). The amount of UCP which interacts with the molecule or the amount which does not bind to the molecule may then be quantitated to determine whether the molecule binds to UCP. A surface having a known molecule that binds to UCP such as a commercially available monoclonal antibody immobilized thereto may serve as a positive control. Several types of commercially available antibodies are described above.

Screening of molecules of the invention, also can be carried out utilizing a competition assay. If the molecule being tested competes with the known monoclonal antibody, as shown by a decrease in binding of the known monoclonal antibody, then it is likely that the molecule and the known monoclonal antibody bind to the same, or a closely related, epitope. Still another way to determine whether a molecule has the specificity of the known monoclonal antibody is to pre-incubate the known monoclonal antibody with the target with which it is normally reactive, and then add the molecule being tested to determine if the molecule being tested is inhibited in its ability to bind the target. If the molecule being tested is inhibited then, in all likelihood, it has the same, or a functionally equivalent, epitope and specificity as the known monoclonal antibody.

In one embodiment the binding peptides useful according to the invention are antibodies or functionally active antibody fragments. Antibodies are well known to those of ordinary skill in the science of immunology. Many of the binding peptides described herein are available from commercial sources as intact functional antibodies, as described above. As used herein, the term "antibody" means not only intact antibody molecules but also fragments of antibody molecules retaining specific binding ability. Such fragments are also well known in the art. In particular, as used herein, the term "antibody" means not only intact immunoglobulin molecules but also the well-known active fragments $F(ab')_2$, and Fab. $F(ab')_2$, and Fab fragments which lack the Fc fragment of intact antibody (Wahl et al., *J. Nucl. Med.* 24:316-325 (1983)).

According to one embodiment, the peptide of the invention is an intact soluble monoclonal antibody in an isolated form or in a pharmaceutical preparation. An intact soluble monoclonal antibody, as is well known in the art, is an assembly of polypeptide chains linked by disulfide bridges. Two principle polypeptide chains, referred to as the light chain and heavy chain, make up all major structural classes (isotypes) of antibody. Both heavy chains and light chains are further divided into subregions referred to as variable regions and constant regions. As used herein the term "monoclonal antibody" refers to a homogenous population of immunoglobulins which specifically bind to an epitope (i.e. antigenic determinant), e.g., of cell wall/plasma membrane UCP, chloroplast UCP etc.

The binding peptides may also be functionally active antibody fragments. Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. An isolated $F(ab')_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')$_2$ and Fv are used consistently with their standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)].

The inhibitors of the invention are isolated molecules. An isolated molecule is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations or sequencing if the molecular species is a nucleic acid, peptide, or polysaccharide. Because an isolated molecular species of the invention may be admixed with a pharmaceutically-acceptable carrier in a pharmaceutical preparation, the molecular species may comprise only a small percentage by weight of the preparation. The molecular species is nonetheless substantially pure in that it has been substantially separated from the substances with which it may be associated in living systems.

A inhibitors of fatty acid metabolism may also be expression inhibitors. An expression inhibitor as used herein is a molecule that knocks down expression of a gene encoding a protein that plays a positive role in fatty acid metabolism. Thus, the invention also features the use of small nucleic acid molecules, including antisense nucleic acids and short interfering nucleic acid (siNA), the latter include, for example: microRNA (miRNA), short interfering RNA (siRNA), double-stranded RNA (dsRNA), and short hairpin RNA (shRNA) molecules to knockdown expression of proteins such as enzymes involved in fatty acid metabolism. An siNA of the invention can be unmodified or chemically-modified. An siNA of the instant invention can be chemically synthesized, expressed from a vector or enzymatically synthesized. The instant invention also features various chemically-modified synthetic short interfering nucleic acid (siNA) molecules capable of modulating gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. The siNA molecules of the instant invention provide useful reagents and methods for a variety of therapeutic applications.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al, 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2' amino, 2'-C-allyl, 2'-fluoro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565 568; Pieken et al. Science, 1991, 253, 314317; Usman and Cedergren, Trends in Biochem. Sci., 1992, 17, 334 339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., molecule comprises one or more chemical modifications.

In one embodiment, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 25 nucleotides, and each strand comprises at least about 19 nucleotides that are complementary to the nucleotides of the other strand.

In some embodiments an siNA is an shRNA, shRNA-mir, or microRNA molecule encoded by and expressed from a genomically integrated transgene or a plasmid-based expression vector. Thus, in some embodiments a molecule capable of inhibiting mRNA expression, or microRNA activity, is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems.

In another embodiment, a small interfering nucleic acid of the invention is expressed in plant or fungal cells using a plant, fungal or mammalian expression vectors. The recombinant expression vector may be capable of directing expression of the nucleic acid preferentially in a particular cell type (e.g., tissue-specific regulatory elements are used to express the nucleic acid). Tissue specific regulatory elements are known in the art.

Other inhibitor molecules that can be used include sense and antisense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat Med. 4(8):967-71, 1998). For example, neoplastic reversion was obtained using a ribozyme targeted to an H-Ras mutation in bladder carcinoma cells (Feng et al., Cancer Res. 55(10):2024-8, 1995). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6): 643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

Antisense nucleic acids include modified or unmodified RNA, DNA, or mixed polymer nucleic acids, and primarily function by specifically binding to matching sequences resulting in modulation of peptide synthesis (Wu-Pong, November 1994, BioPharm, 20-33). Antisense nucleic acid binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, Crit. Rev. in Oncogenesis 7, 151-190).

As used herein, the term "antisense nucleic acid" describes a nucleic acid that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4):307-17, 1991; Knudsen and Nielson Nucleic Acids Res. 24(3):494-500, 1996; Taylor et al., Arch. Surg. 132(11):1177-83, 1997). Minor-groove binding polyamides can bind in a sequence-specific manner to DNA targets and hence may represent useful small molecules for future suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). In some cases suppression strategies have led to a reduction in RNA levels without a concomitant reduction in proteins, whereas in others, reductions in RNA have been mirrored by reductions in protein.

The diverse array of suppression strategies that can be employed includes the use of DNA and/or RNA aptamers that can be selected to target, for example, a protein of interest such as enzymes involved in fatty acid metabolism.

Many embodiments of the invention employ single-stranded RNA molecules containing an inverted repeat region that causes the RNA to self-hybridize, forming a hairpin structure. shRNA molecules of this type may be encoded in RNA or DNA vectors. The term "encoded" is used to indicate that the vector, when acted upon by an appropriate enzyme, such as an RNA polymerase, will give rise to the desired shRNA molecules (although additional processing enzymes may also be involved in producing the encoded shRNA molecules). As described herein, vectors comprising one or more encoded shRNAs may be transfected into cells ex vivo, and the cells may be introduced into mammals. The expression of shRNAs may be constitutive or regulated in a desired manner.

A double-stranded structure of an shRNA is formed by a single self-complementary RNA strand. RNA duplex formation may be initiated either inside or outside the cell. Inhibition is sequence-specific in that nucleotide sequences corresponding to the duplex region of the RNA are targeted for genetic inhibition. shRNA constructs containing a nucleotide sequence identical to a portion, of either coding or non-coding sequence, of the target gene are preferred for inhibition. RNA sequences with insertions, deletions, and single point mutations relative to the target sequence have also been found to be effective for inhibition. Because 100% sequence identity between the RNA and the target gene is not required to practice the present invention, the invention has the advantage of being able to tolerate sequence variations that might be expected due to genetic mutation, strain polymorphism, or evolutionary divergence. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50.degree. C. or 70.degree. C. hybridization for 12-16 hours; followed by washing). In certain preferred embodiments, the length of the duplex-forming portion of an shRNA is at least 20, 21 or 22 nucleotides in length, e.g., corresponding in size to RNA products produced by Dicer-dependent cleavage. In certain embodiments, the shRNA construct is at least 25, 50, 100, 200, 300 or 400 bases in length. In certain embodiments, the shRNA construct is 400-800 bases in length. shRNA constructs are highly tolerant of variation in loop sequence and loop size.

The term "percent identical" refers to sequence identity between two amino acid sequences or between two nucleotide sequences. Percent identity can be determined by comparing a position in each sequence which may be aligned for purposes of comparison. Expression as a percentage of identity refers to a function of the number of identical amino acids or nucleic acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

An endogenous RNA polymerase of the cell may mediate transcription of an shRNA encoded in a nucleic acid construct. The shRNA construct may also be synthesized by a bacteriophage RNA polymerase (e.g., T3, T7, SP6) that is expressed in the cell. In preferred embodiments, expression of an shRNA is regulated by an RNA polymerase III promoters; such promoters are known to produce efficient silencing. A U6 snRNA leader sequence may be appended to the primary transcript; such leader sequences tend to increase the efficiency of sub-optimal shRNAs while generally having little or no effect on efficient shRNAs. For transcription from a transgene in vivo, a regulatory region (e.g., promoter, enhancer, silencer, splice donor and acceptor, polyadenylation) may be used to regulate expression of the shRNA strand (or strands). Inhibition may be controlled by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. The use and production of an expression construct are known in the art (see also WO 97/32016; U.S. Pat. Nos. 5,593,874, 5,698,425, 5,712,135, 5,789,214, and 5,804,693; and the references cited therein).

Further information on the optimization of shRNA constructs may be found, for example, in the following references: Paddison, P. J., A. A. Caudy, and G. J. Hannon, Stable suppression of gene expression by RNAi in mammalian cells. Proc Natl Acad Sci USA, 2002. 99 (3): p. 1443-8; 13. Brummelkamp, T. R., R. Bernards, and R. Agami, A System for Stable Expression of Short Interfering RNAs in Mammalian Cells. Science, 2002. 21: p. 21; Kawasaki, H. and K. Taira, Short hairpin type of dsRNAs that are controlled by tRNA (Val) promoter significantly induce RNAi-mediated gene silencing in the cytoplasm of human cells. Nucleic Acids Res, 2003. 31 (2): p. 700-7; Lee, N. S., et al., Expression of small interfering RNAs targeted against HIV-1 rev transcripts in human cells. Nat Biotechnol, 2002. 20 (5): p. 500-5; Miyagishi, M. and K. Taira, U6 promoter-driven siRNAs with four uridine 3' overhangs efficiently suppress targeted gene expression in mammalian cells. Nat Biotechnol, 2002. 20 (5): p. 497-500; Paul, C. P., et al., Effective expression of small interfering RNA in human cells. Nat Biotechnol, 2002. 20 (5): p. 505-8.

An siNA useful in the invention will generally be designed to have partial or complete complementarity with one or more target genes (i.e., complementarity with one or more transcripts of one or more target genes). The target gene may be a gene derived from the cell, an endogenous gene, a transgene, or a gene of a pathogen which is present in the cell after infection thereof. Depending on the particular target gene, the nature of the siNA and the level of expression of siNA (e.g. depending on copy number, promoter strength) the procedure may provide partial or complete loss of function for the target gene. Quantitation of gene expression in a cell may show similar amounts of inhibition at the level of accumulation of target mRNA or translation of target protein.

"Inhibition of gene expression" refers to the absence or observable decrease in the level of protein and/or mRNA product from a target gene. "Specificity" refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. One preferred method of assessing the function of an siNA of the invention involves determining changes in fat accumulation levels within a cell Depending on the assay, quantitation of the amount of gene expression allows one to determine a degree of inhibition which is greater than 10%, 33%, 50%, 90%, 95% or 99% as compared to a cell not treated according to the present invention. As an example, the efficiency of inhibition may be determined by assessing the amount of gene product in the cell: mRNA may be detected with a hybridization probe having a nucleotide sequence outside the region used for the inhibitory double-stranded RNA, or translated polypeptide may be detected with an antibody raised against the polypeptide sequence of that region.

As disclosed herein, the present invention is not limited to any type of target gene or nucleotide sequence. The following possible target genes are listed for illustrative purposes: specific examples of enzymes within the fatty acid metabolism pathway including 2,4-dienoyl-CoA reductase, 2,4-dienoyl-CoA isomerase, and butyryl dehydrogenase, as well as UCP.

In certain embodiments, a vector system for introducing siNA constructs into cells are retroviral vector systems, such as lentiviral vector systems. Lentiviral systems permit the delivery and expression of siNA constructs to both dividing and non-dividing cell populations in vitro and in vivo. Examples of Lentiviral vectors are those based on HIV, FIV and EIAV. See, e.g., Lois, C., et al., Germline transmission and tissue-specific expression of transgenes delivered by lentiviral vectors. Science, 2002. 295 (5556): p. 868-72. Most viral systems contain cis-acting elements necessary for packaging, while trans-acting factors are supplied by a separate plasmid that is co-transfected with the vector into a packaging cell line. In certain embodiments, a highly transfectable 293 cell line may be used for packaging vectors, and viruses may be pseudotyped with a VSV-G envelope glycoprotein for enhanced stability and to provide broad host range for infection. In certain aspects, the invention provides novel vectors adapted for use with siNA expression cassettes. The type of vector and promoters to be employed should be selected, in part, depending on the organism and cell type to be affected.

In certain embodiments, retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. A retroviral plasmid vector may be employed to transduce packaging cell lines to form producer cell lines. Examples of packaging cells which may be transfected include, but are not limited to, the PE501, PA317, R-2, R-AM, PA12, T19-14.times., VT-19-17-H2, RCRE, RCRIP, GP+E-86, GP+envAml2, and DAN cell lines as described in Miller, Human Gene Therapy 1:5-14 (1990), which is incorporated herein by reference in its entirety. The vector may transduce the packaging cells through any means known in the art.

Essentially any method for introducing a nucleic acid construct into cells may be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle may be used to accomplish both efficient introduction of an expression construct into the cell and transcription of the encoded shRNA. Other methods known in the art for introducing nucleic acids to cells may be used, such as lipid-mediated carrier transport, chemical mediated transport, such as calcium phosphate, and the like. Thus the siNA-encoding nucleic acid construct may be introduced along with components that perform one or more of the following activities: enhance RNA uptake by the cell, promote annealing of the duplex strands, stabilize the annealed strands, or otherwise increase inhibition of the target gene.

Thus, the present invention provides methods and compositions for the expression of nucleic acids including siNA in plants. The present invention contemplates that any method of transfection that is suitable for transfection of plants, plant tissues, and plant cells may be used with the present invention. Such methods include, but are not limited to, *Agrobacterium*-mediated transformation (e.g., Komari et al., Curr. Opin. Plant Biol., 1:161 [1998]), particle bombardment mediated transformation (e.g., Finer et al., Curr. Top. Microbiol. Immunol., 240:59 [1999]), protoplast electroporation (e.g., Bates, Methods Mol. Biol., 111:359 [1999]), viral infection (e.g., Porta and Lomonossoff, Mo. Biotechnol. 5:209 [1996]), microinjection, and liposome injection. Standard molecular biology techniques are common in the art (See e.g., Sambrook, J. et al., *Molecular Cloning: A Laboratory Manual*, $2^{nd}$ ed., Cold Spring Harbor Laboratory Press, New York [1989]). For example, in one embodiment of the present invention tobacco or *arabidopsis* is transformed with a gene encoding UCP using *Agrobacterium*.

A wide variety of promoters have been isolated from plants, which are functional not only in the cellular source of the promoter, but also in numerous other plant species. There are also other promoters (e.g., viral and Ti-plasmid) which can be used. For example, these promoters include promoters from the Ti-plasmid, such as the octopine synthase promoter, the nopaline synthase promoter, the mannopine synthase promoter, promoters from other open reading frames in the T-DNA, such as ORF7, etc. Promoters isolated from plant viruses include the 35S promoter from cauliflower mosaic virus (CaMV). Promoters that have been isolated and reported for use in plants include ribulose-1,3-biphosphate carboxylase small subunit promoter, phaseolin promoter, etc.

Using any of the above gene transfer techniques, an expression vector harboring the gene of interest is transformed into the desired plant sample to achieve temporary or prolonged expression of the gene. Any suitable expression system may be used, so long as it is capable of undergoing transformation and expressing of the gene of interest in the host. In one embodiment of the present invention, a pET vector (Novagen, Madison, Wis.), or a pBI vector (Clontech, Palo Alto, Calif.) is used as the expression vector. In some embodiments an expression vector further encoding a green fluorescent protein (GFP) is used to allow simple selection of transfected cells and to monitor expression levels. Examples of such vectors include Clontech's "Living Colors Vectors" pEYFP and pEYFP-C1. The EYFP gene is codon optimized for high expression in plant cells.

Site-specific recombinases catalyze recombination reactions between two nucleotide sequences referred to as recombination sites. If such recombination sites are integrated into genomic DNA, depending on the orientation of these sites relative to each other, i.e., direct or inverted, the intervening genomic DNA sequence can be either inverted or excised by certain site-specific recombinases. If the recombination sites are on two different chromosomes, some of the recombinases can catalyze the exchange of chromosomal fragments. Thus, site-specific recombination reactions have the potential to have substantial practical applications in genetic engineering.

Techniques for targeted insertion and the deletion of DNA from transgenic plant chromosomes are useful in the methods of the invention. The Cre-lox recombination system may be used for the controlled excision of DNA fragments from the nuclear and chloroplast genomes, and for the targeted insertion of DNA into specific sites in the nuclear genome. The Cre-lox system provides an efficient and precise tool for plant genetic manipulations. The FLP/FRT system from the *Saccharomyces cerevisiae*, can recognize and recombine FRT sites located in a plasmid molecule in several plants.

Once the cells accumulate or store fatty acid the fatty acids may be collected from the plant cell or fungus. Many methods for collecting the fatty acids from cells are known in the art.

For instance, the fatty acids may be collected directly in the form of fatty acids or may be processed into other materials such as biofuels prior or after partial or total separation from the other components of the cell.

The fatty acids produced in the methods of the invention may be further processed to produce a biofuel. Thus, the biofuels can be generated from plants or fungi that have been treated with a compound that alters metabolism in a manner that allows accumulation of fatty acids. Such modified plants and fungi contain high amounts of vegetable oil, i.e. corn, palm, soybean, algae, *jatropha*, or *pongamia pinnata*. A biofuel as used herein is a solid, liquid or gaseous fuel obtained from a biological material and can be any fuel, fuel additive, aromatic, and/or aliphatic compound derived from a biomass starting material such as algae, corn, switchgrass etc. The biofuels of the invention are produced from plants or fungus. Biofuels include for instance, syngas and biodiesel.

The fatty acids produced by the metabolic disruption of plants or fungus can be processed in many different ways to produce biofuels. For instance, the fatty acids may be heated, to reduce the viscosity. The reduced viscosity fatty acids can be burned directly in a diesel engine. Alternatively they may be chemically processed to produce fuels such as biodiesel.

Syngas (synthesis gas) is a fuel that is a mixture of carbon monoxide and hydrogen that is produced by partial combustion of biomass. The combustion includes an amount of oxygen that is not sufficient to convert the biomass completely to carbon dioxide and water. The biomass may be dried, and/or pyrolyzed prior to the partial combustion. The syngas may be in some instances more efficient than direct combustion of the original biofuel because more of the energy contained in the fuel is extracted. Syngas may be burned directly in internal combustion engines or turbines.

Biodiesel is produced from fats using a process known as transesterification and is a liquid similar in composition to fossil/mineral diesel. Its chemical name is fatty acid methyl (or ethyl) ester. Oils are mixed with sodium hydroxide and methanol (or ethanol) and the chemical reaction produces biodiesel and glycerol. One part glycerol is produced for every 10 parts biodiesel.

A variety of methods for processing of the oil loaded cells of the invention into biodiesel are known in the art and any such known method may be used in the practice of the instant invention. For example, the algae may be harvested, separated from the liquid medium, lysed and the oil content separated. The oil stored inside the plant cell or algae or fungus can be recovered in several relatively simple ways, including solvents, heat, and/or pressure. Other methods involve depolymerizing, such as biologically breaking the walls of the algal cell and/or oil vesicles, if present, to release the oil from the oil-producing algae.

In one example, fatty acids can be extracted in an oil extraction bioreactor which may be connected to the algae growth reservoirs. Within the oil extraction bioreactor the cell walls and algal oil vesicles of the oil-producing algae can be biologically ruptured to yield an algal oil and algal residue. An active agents can be used for releasing algae energy stores, i.e. enzymes such as cellulase or glycoproteinase, structured enzyme arrays or system such as a cellulosome, a viral gent such as a virus or viral lysate, or a combination thereof. A cellulase is an enzyme that breaks down cellulose, especially in the wall structures, and a cellulosome is an array or sequence of enzymes or cellulases which is more effective and faster than a single enzyme or cellulase. In both cases, the enzymes break down the cell wall and/or oil vesicles and release oil or starch from the cell. Cellulases used for this purpose may be derived from fungi, bacteria, or yeast. Non-limiting examples of each include cellulase produced by fungus *Trichoderma reesei* and many genetic variations of this fungus, cellulase produced by bacteria genus *Cellulomonas*, and cellulase produced by yeast genus *Trichosporon*. A glycoproteinase provides the same function as a cellulase, but is more effective on the cell walls of microalgae, many of which have a structure more dependent on glycoproteins than cellulose.

In addition, a large number of viruses exist which invade and rupture algae cells, and can thereby release the contents of the cell. Specific examples of such viruses include the *chlorella* virus PBCV-1 (Paramecium Bursaria Chlorella Virus) which is specific to certain *Chlorella* algae, and cyanophages such as SM-1, P-60, and AS-1 specific to the blue-green algae *Synechococcus*.

Mechanical crushing, for example, an expeller or press, a hexane or butane solvent recovery step, supercritical fluid extraction, can also be useful in extracting the oil from oil vesicles of the oil-producing algae. Alternatively, mechanical approaches can be used in combination with biological agents in order to improve reaction rates and/or separation of materials.

Once the oil has been released from the cells it can be recovered or separated from the cellular debris, e.g. cellular residue, oil, enzyme, by-products, etc by sedimentation or centrifugation. The recovered oil can be collected and directed further processing.

The oil produced in these methods will be rich in triglycerides. A triglyceride consists of three fatty acid chains, one attached to each of the three carbon atoms in a glycerol backbone. This form of oil can be burned directly or converted into a biodiesel fuel. Such oils may be converted into biodiesel using well-known methods. One process for converting the triglyceride to biodiesel is transesterification, and includes reacting the triglyceride with alcohol or other acyl acceptor to produce free fatty acid esters and glycerol. The free fatty acids are in the form of fatty acid alkyl esters (FAAE). Standard transesterification processes involve an alkaline catalyzed transesterification reaction between the triglyceride and an alcohol, typically methanol. The fatty acids of the triglyceride are transferred to methanol, producing alkyl esters (biodiesel) and releasing glycerol. The glycerol is removed and may be used for other purposes.

In contrast to batch reaction methods (e.g., J. Am. Oil Soc. 61:343, 1984), the Connemann process (see, e.g., U.S. Pat. No. 5,354,878, incorporated herein by reference) utilizes continuous flow of the reaction mixture through reactor columns, in which the flow rate is lower than the sinking rate of glycerine. This results in the continuous separation of glycerine from the biodiesel. The reaction mixture may be processed through further reactor columns to complete the transesterification process. Residual methanol, glycerine, free fatty acids and catalyst may be removed by aqueous extraction. The Connemann process is well-established for production of biodiesel from plant sources such as rapeseed oil. Any method known in the art for producing biodiesel from triglyceride containing oils may be utilized, for example as disclosed in U.S. Pat. Nos. 4,695,411; 5,338,471; 5,730,029; 6,538,146; 6,960,672, each incorporated herein by reference. Alternative methods that do not involve transesterification may also be used. For example, by pyrolysis, gasification, or thermochemical liquefaction (see, e.g., Dote, 1994, Fuel 73:12; Ginzburg, 1993, Renewable Energy 3:249-52; Benemann and Oswald, 1996, DOE/PC/93204-T5).

Transesterification often uses a simple alcohol, typically methanol derived from petroleum. When methanol is used the resultant biodiesel is called fatty acid methyl ester (FAME) and most biodiesel sold today, especially in Europe, is FAME. However, ethanol can also be used as the alcohol in transesterification, in which case the biodiesel is fatty acid ethyl ester (FAEE). In the U.S., the two types are usually not distinguished, and are collectively known as fatty acid alkyl esters (FAAE), which as a generic term can apply regardless of the acyl acceptor used. Direct hydrogenation can also be utilized to convert at least a portion of the fatty acids to a biodiesel.

The fatty acids may also be converted to biodiesel by direct hydrogenation. In this process, the products are alkane chains, propane, and water. The glycerol backbone is hydrogenated to propane, so there is substantially no glycerol produced as a byproduct. Furthermore, no alcohol or transesterification catalysts are needed. All of the biomass can be used as feed for the oil-producing algae with none needed for fermentation to produce alcohol for transesterification. The resulting alkanes are pure hydrocarbons, with no oxygen, so the biodiesel produced in this way has a slightly higher energy content than the alkyl esters, degrades more slowly, does not attract water, and has other desirable chemical properties.

Optionally, the algae may be used as a source of waste disposal while also producing enhanced quantities of fatty acids. For instance, U.S. Pat. No. 7,208,530 describes such methods. Additionally, GreenFuel Technologies Corporation uses algae to absorb smokestacks flue gases and produce biofuels such as biodiesel, biogas and a dry fuel comparable to coal.

As used herein, the term "dissipation of cellular proton motor force" refers to the relative amount of protons in the cell. It can be assessed by measuring cell wall/plasma, chloroplast, or mitochondrial membrane potential depending on the UCP being studied. As used herein "cell wall/plasma membrane potential" is the pressure on the inside of the cell wall/plasma membrane measured relative to the extracellular fluid which is created by the generation and dissipation of charge within the cell. The "chloroplast membrane potential" is the pressure on the inside of the chloroplast membrane measured relative to the cytoplasma which is created by the generation and dissipation of charge within the chloroplast. The cell wall/plasma or chloroplast membrane potential is maintained by the energy generating system of the cell wall/plasma or chloroplast membrane respectively. In most tissues electron transport is coupled to oxidative phosphorylation resulting in the production of ATP from glucose. UCPs can cause the reversible uncoupling of electron transport and oxidative phosphorylation, which leads to a decrease in the mitochondrial membrane potential, or as discovered herein the cell wall/plasma or chloroplast membrane potential.

The absolute levels of the membrane potential vary depending on the cell or tissue type. As used herein an "increase in membrane potential" is an increase relative to the normal status of the cell being examined and results from the prevention of dissipation of proton motor force. "Prevention" as used herein refers to a decrease or reduction in the amount of dissipation that would ordinarily occur in the absence of the stimulus applied according to the methods of the invention to cause coupling. If electron transport and oxidative phosphorylation are normally uncoupled within the membrane of the cell then the baseline potential will be relatively low and when the ATP generating systems are coupled an increase in membrane potential from that baseline level is observed Likewise, a "decrease in membrane potential" is a decrease relative to the normal status of the cell being examined and results from the dissipation of proton motor force. If electron transport and oxidative phosphorylation are normally coupled within the cell then the baseline potential will be relatively high and when the ATP generating systems are uncoupled a decrease in membrane potential from that baseline level is observed.

Changes in membrane potential can be assessed by any method known in the art for making such measurements. For example the membrane potential may be assessed using the well known comet assay, where whole cells are electrophoresed on an agarose gel and examined for the presence of a tail. Alternatively it may be measured using electrodes placed on opposite sides of the membrane. Membrane potential may also be measured cytometrically by incubating cells for approximately 20 minutes at room temperature with a membrane specific fluorescent probe. The aggregation state and consequently the fluorescence emission of fluorescent probe changes as the membrane potential is altered. Flow cytometry permits the examination of more than one, for instance eight, fluorescent markers concurrently.

Each of the compositions of the invention may optionally be associated with a delivery system or vector or may be delivered alone. In its broadest sense, a "vector" is any vehicle capable of facilitating: (1) delivery of a composition to a target cell or (2) uptake of a composition by a target cell, if uptake is important. In general, the vectors useful in the invention are divided into two classes: colloidal dispersion systems and biological vectors.

As used herein, a "colloidal dispersion system" refers to a natural or synthetic molecule, other than those derived from bacteriological or viral sources, capable of delivering to and releasing the active agent to the plant cell. Colloidal dispersion systems include macromolecular complexes, beads, and lipid-based systems including oil-in-water emulsions, micelles, mixed micelles, and liposomes. A preferred colloidal system of the invention is a liposome. Liposomes are artificial membrane vessels. It has been shown that large unilamellar vessels (LUV), which range in size from 0.2-4.0μ can encapsulate large macromolecules within the aqueous interior and these macromolecules can be delivered to cells in a biologically active form (Fraley, et al., *Trends Biochem. Sci.*, 6:77 (1981)).

Lipid formulations for transfection are commercially available from QIAGEN, for example as EFFECTENE™ (a non-liposomal lipid with a special DNA condensing enhancer) and SUPER-FECT™ (a novel acting dendrimeric technology) as well as Gibco BRL, for example, as LIPOFECTIN™ and LIPOFECTACE™, which are formed of cationic lipids such as N-[1-(2, 3 dioleyloxy)-propyl]-N,N, N-trimethylammonium chloride (DOTMA) and dimethyl dioctadecylammonium bromide (DDAB). Methods for making liposomes are well known in the art and have been described in many publications. Liposomes were described in a review article by Gregoriadis, G., *Trends in Biotechnology* 3:235-241 (1985), which is hereby incorporated by reference.

It is envisioned that the Inhibitor may be delivered to the subject in a biological vector which is a nucleic acid molecule which encodes for the Inhibitor such that the Inhibitor is expressed. The nucleic acid encoding the Inhibitor is operatively linked to a gene expression sequence, such as that described above.

The Inhibitor nucleic acid of the invention may be delivered to the cell alone or in association with a vector. In its broadest sense, a "vector" is any vehicle capable of facilitating the transfer of the Inhibitor nucleic acid to the appropriate cells so that the inhibitor can be expressed on the within the cell. Preferably, the vector transports the nucleic acid to the cells with reduced degradation relative to the extent of degradation that would result in the absence of the vector. The vector optionally includes the above-described gene expression sequence to enhance expression of the Inhibitor nucleic acid. In general, the vectors useful in the invention include, but are not limited to, plasmids, phagemids, viruses, other vehicles derived from viral or bacterial sources that have been manipulated by the insertion or incorporation of the Inhibitor nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. An example of virus for certain applications is the adeno-associated virus, a double-stranded DNA virus. The adeno-associated virus can be engineered to be replication-deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions.

Other vectors include plasmid vectors. Plasmid vectors have been extensively described in the art and are well-known to those of skill in the art. See e.g., Sambrook et al., "Molecular Cloning: A Laboratory Manual," Second Edition, Cold Spring Harbor Laboratory Press, 1989. These plasmids having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well-known to those of ordinary skill in the art. Additionally, plasmids may be custom designed using restriction enzymes and ligation reactions to remove and add specific fragments of DNA.

Other exemplary compositions that can be used to facilitate uptake by a target cell of the compositions of the invention include calcium phosphate and other chemical mediators of intracellular transport, microinjection compositions, electroporation and homologous recombination compositions (e.g., for integrating a composition of the invention into a preselected location within the target cell chromosome).

As used herein the term "transgenic" when used in reference to a plant or fruit (i.e., a "transgenic plant" or "transgenic fruit") refers to a plant or fruit that contains at least one heterologous gene in one or more of its cells.

As used herein, the term "sample" is used in its broadest sense. In one sense it can refer to a plant cell or tissue. In another sense, it is meant to include a specimen or culture obtained from any source, as well as biological and environmental samples. Biological samples may be obtained from plants or animals and encompass fluids, solids, tissues, and gases. Environmental samples include environmental material such as surface matter, soil, water, and industrial samples. These examples are not to be construed as limiting the sample types applicable to the present invention.

The words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

As used herein, the term "selectable marker" refers to the use of a gene that encodes an enzymatic or other detectable activity (e.g., luminescence, fluorescence, or radioactivity) that confers the ability to grow in medium lacking what would otherwise be an essential nutrient. A selectable marker may also confer resistance to an antibiotic or drug upon the cell in which the selectable marker is expressed. Selectable markers may be "dominant"; a dominant selectable marker encodes an enzymatic or other activity (e.g., luminescence, fluorescence, or radioactivity) that can be detected in any cell line.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The following examples are provided to illustrate specific instances of the practice of the present invention and are not to be construed as limiting the present invention to these examples. As will be apparent to one of ordinary skill in the art, the present invention will find application in a variety of compositions and methods.

EXAMPLES

Typically, the preferred plants for efficient and clean production of alternative sources of energy are rich in sucrose and efficient in sucrose storage as demonstrated by the effective use of sugar cane in Brazil. While effective in climates such as Brazil, the challenge is that sugar cane will only grow in tropical environments. Oil producing plants such as algae have also been proposed as sources for alternative energy. The methods of the invention involve processes for directly increasing the production of oil in plants through metabolic disruption to efficiently increase oil accumulation and/or storage in the plant. We have demonstrated herein that by modifying fuel metabolism, specifically by inhibiting fatty acid metabolism, in plants, we can increase the selective storage of oils. In some specific examples presented below, we have used the golden algae *Schizochytrium* as a model organism. In addition, we have used various seeds, including cucumber, soybeans, and corn and plants, including *Jatropha*. An advantages of the approach is the diversity of plants that can become fuel sources when processed according to the methods of the invention.

Methods:
Growth and Maintenance of *Schizochytrium*

The media used for maintaining *Schizochytrium* is 790 BY+ medium. It is prepared as follows. 1.0 g of yeast extract, 1.0 g of Peptone and 5.0 g of D+ Glucose were added to an autoclaveable glass bottle with 1 L of sterile sea water. The mixture was autoclaved at 121° C. for 15 minutes.

*Schizochytrium* were removed from liquid nitrogen storage tank. 100 mL of 790 BY+ medium was added to a 250 mL Erlenmeyer flask. The cells were thawed in at 37° C. water bath until completely liquid and then transferred to the 250 mL Erlenmeyer flask. A foam stopper was placed in the flask opening and the flask was placed on a shaker stirrer. Once every 7 days 2 mL of the *Schizochytrium* were transferred into a new 250 mL Erlenmeyer flask containing 100 mL of 790 BY+ medium.

Staining *Schizochytrium* using Oil Red O

Oil Red O is a selective stain to confirm the presence of oil in a cell or organelle. Oil red O is the accepted method for determining if the contents of organelles such as the glyoxosome are filled with oil. A culture of *Schizochytrium* was obtained as discussed above. The *Schizochytrium* was vigorously stirred and carefully placed (10 µL) onto a microscope slide. 10 µL of Oil Red O was added directly to the *Schizochytrium* on the microscope slide and pipetted up and down to completely mix. The cover slip was placed over the drop on the microscope slide and allowed to incubate at room temperature for 5 minutes. The material was examined under normal light microscope at 40 to 63× magnification.

Staining of *Schizochytrium* using Lysosensor, DCF-da; or Mitotracker

Lysosensor fluoresces as a function of organellar acidity, a reflection of fatty acids; DCF-da fluoresces as a function of reactive intermediates, especially H2O2; Mitotracker Red fluoresces as a function of mitochondrial membrane potential.

For flow cytometric analysis, the desired number of flow tubes were labeled (4 per treatment group). For microscopy, the desired number of microscope slides were labeled (2 per treatment). A culture of *Schizochytrium* was obtained. Count *Schizochytrium* and resuspend to obtain a concentration of $1 \times 10^6$ cells per 100 µL of PBS. $5 \times 10^6$ cells per treatment group were used for flow cytometry and $2 \times 10^6$ were used for microscopy. 100 µL of resuspended cells were added to each of wells to be stained. Either 1 µL of Lysosensor, 1 µL of Mitotracker, or 1 µL of DCFda was added to each of the "stain" well and vigorously stirred. The mixture was allowed to incubate in a dark place for 20 minutes at room temperature. 100 µL of PBS was added to each well and centrifuged at 1000 rpm for 5 minutes. The supernatant was flicked into the sink and the pellet resuspend in 100 µL of PBS. For flow cytometry, all 100 µL of stained cells were transferred into the appropriate flow tube. For microscopy, 10 µL of suspension was added to the appropriate microscope slide and covered with a cover slip. The sample was run on a flow cytometer (either a Coulter Excel or a Coulter FC500) using FL1 for Lysosensor Green or DCF-da or FL2 for Mitotracker Red or FL1 for MITO tracker Green or FL2 for Mitotracker Red. For microscopy FITC channel was used.

Flow Cytometry

*Schizochytrium* or *chlamydomonas* were harvested, counted, and resuspended at $10^6$ cells/100 µl of PBS containing 2.5% fetal calf serum in preparation for flow cytometric analysis. Lysosensor dyes were used to detect fatty acids in glyoxosomes or oil droplets. Mitochondrial membrane potential was assessed using Mitotracker Red (CM-H₂XROS, BD Pharmingen). The cells were resuspended in PBS containing 2.5% fetal calf serum containing a final concentration of 0.5 micromolar Mitotracker dye. The cells were incubated at 37° for 20 minutes, washed twice in PBS containing 2.5% fetal calf serum and analyzed flow cytometrically. Data were acquired on a Coulter Excel flow cytometer (Coulter, Hialeah, Fla.) and analyzed with FloJo software. The Coulter Excel flow cytometer has a single excitation wavelength (488 nm) and band filters for PE (575 nm), FITC (525 nm) and Red613 (613 nm) that was used to analyze the stained cells. Each sample population was classified for cell size (forward scatter) and complexity (side scatter), gated on a population of interest and evaluated using 30,000 cells.

Cell Counting

Cells were harvested and resuspended in 1 mL of sea-water medium or Phosphate Buffered Saline (PBS) supplemented with 2.5% FBS, and 5 µL of the cell suspension. Live cells were counted using a hemocytometer and the following calculation was used to determine cell number: Average # of Cells×Dilution×$10^4$.

Preparation of Cell for Staining

For staining protocols, between $0.5 \times 10^6$ and $1.0 \times 10^6$ cells were used. Cells were harvested by centrifugation for 5 minutes at 300×g, washed with PBS/2.5% FBS, and resuspended into PBS/2% FBS for staining. Cells were plated into wells of a labeled 96-well plate in 100 µL of PBS/2.5% FBS.

Cell Surface Staining

Cells were stained with antibodies to uncoupling proteins (anti-UCP2 antibody) (Alpha Diagnostic International). Antibodies for both the isotype control and actual stain were added to the cell suspension, mixed, and then placed on ice for and incubation of 25 minutes in the dark. Subsequently the cells were centrifuged at 300×g for 5 minutes and the supernatant removed. The cells were washed one time with 100 µL of PBS/2.5% FBS and then transferred into flow cyotmetric tubes containing 500 µL of PBS/2.5% FBS for analysis.

Metabolic Activity Assay

Cells were prepared as previously described. The specific metabolic dye Lysosensor or Mitotracker Red was added and mixed into the cell suspension. This plate was then placed into the 37° incubator for a 20-minute incubation. After incubation, the cells were centrifuged at 300×g for 5 minutes, and the supernatant was removed. The cells were then washed once with PBS/2.5% FBS and transferred into flow cytometric tubes containing 500 µL of PBS/2.5% FBS for analysis Statistical Analysis, Percents, and Geometric Mean Values Percents: Gating is a tool provided by FloJo software and allows for the analysis of a certain population of cells. Gating around both the live and dead cell populations giveC a percent of the cell numbers that was in each population. After the gates were drawn, a percent value of dead cells was calculated by taking the number of dead cells divided by the number of total cells and multiplying by one hundred.

Standard Error: When experiments were done in triplicate, a standard error of the mean value was determined using the Excel program (Microsoft). This identified the value given for the error bars seen on some figures.

Example 1

Fatty Acid Accumulation in *Schizochytrium*

It was discovered that *Schizochytrium*, an algae like fungus accumulates or stores more fatty acids when treated with a fatty acid metabolism inhibitor, Oxamate, than untreated *Schizochytrium*. The results are shown in FIG. 1. The histograms depict quantities of Lysosensor as a measurement of fatty acid content in oil bodies, glyoxosomes, or lipid laden-organelles. Fl1 is fluorescence resulting from Lysosensor dye. Interestingly, the lowest concentration of oxamate was the most effective at producing high levels of fatty acid accumulation.

Figure 2:
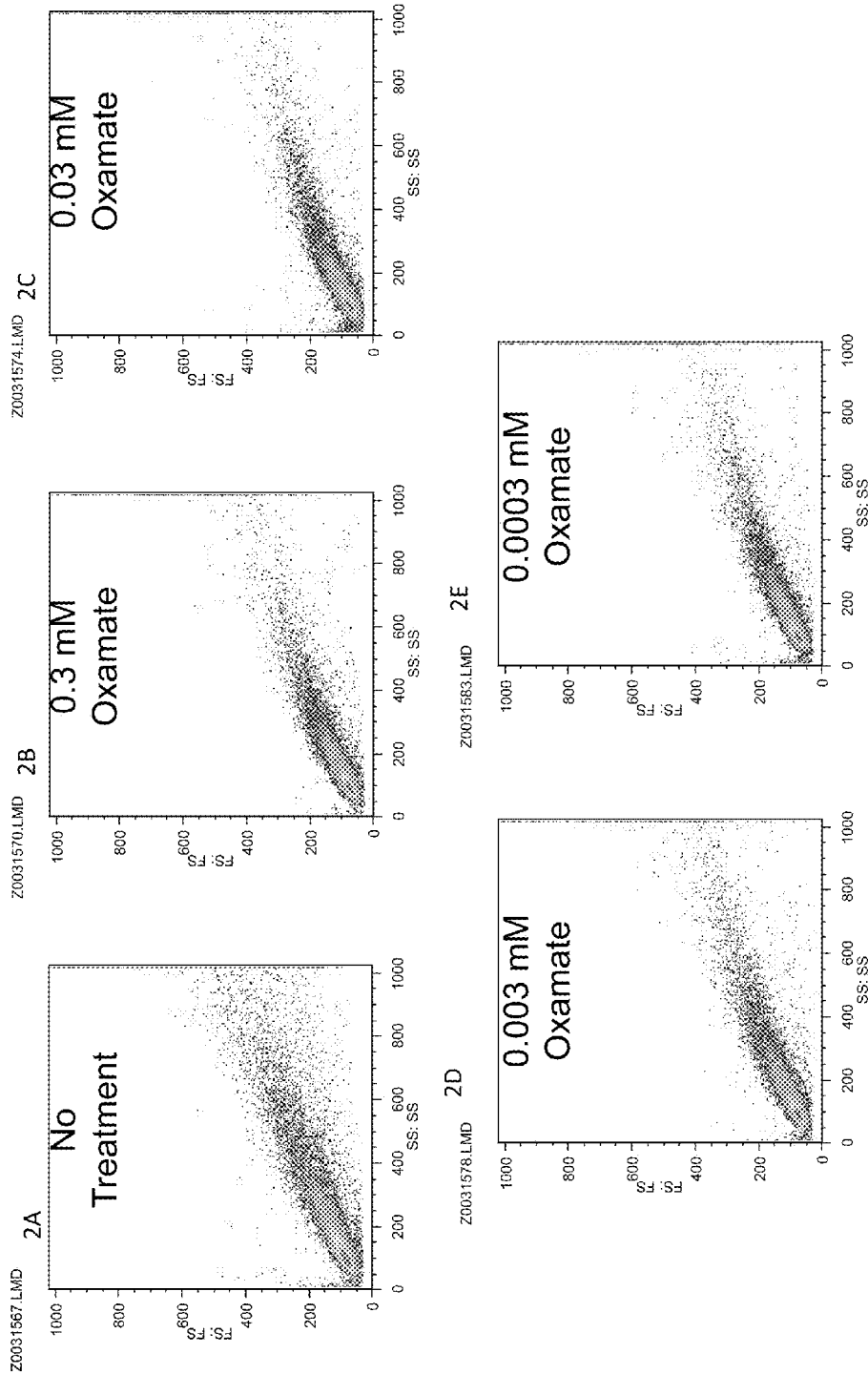
FIG. 2 is a set of dot plots of forward (fsc indicates size) versus side scatter (ssc, a measure of granularity) following treatment with oxamate (FIGS. 2B-2E) or untreated (FIG. 2A) in the same experiment as FIG. 1.

Dot plots of forward (fsc indicates size) versus side scatter (ssc, a measure of granularity) for each of the treatment groups of FIG. 1 were examined. Following treatment with oxamate (FIGS. 2B-2E) or untreated (FIG. 2A) cells were examined by flow cytometry in the same experiment as FIG. 1.

Figure 3:
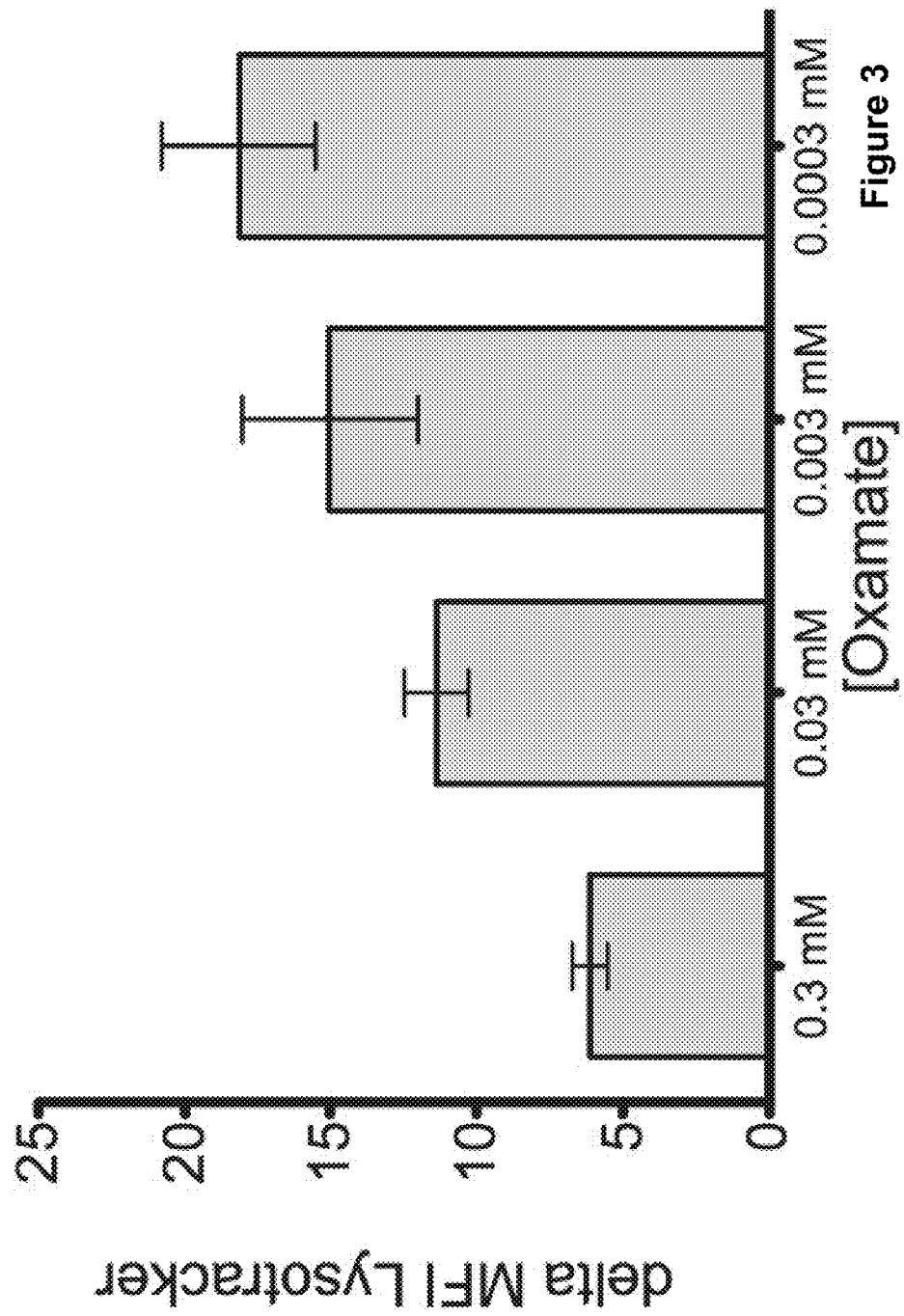
FIG. 3 shows the relative increase in Lysosensor from FIGS. 1 and 2 appears to be inversely correlated with fatty acid content and Oxamate treatment. However, at higher concentrations of Oxamate, had a significantly increased percentage of cell death.

In order to determine why the lowest dose of oxamate was the most effective in producing high fatty acid accumulation, cell death was examined. The bar graph in FIG. 3 depicts the increase in geometric mean of fluorescence in the treated group minus the untreated. The relative increase in Lysosensor from FIGS. 1 and 2 appears to be inversely correlated with fatty acid content and Oxamate treatment (FIG. 3). However, at higher concentrations, oxamate, caused a significantly increased percentage of cell death. Thus, lower doses are sufficient to produce activity and associated with lower toxicity.

Figure 4A:
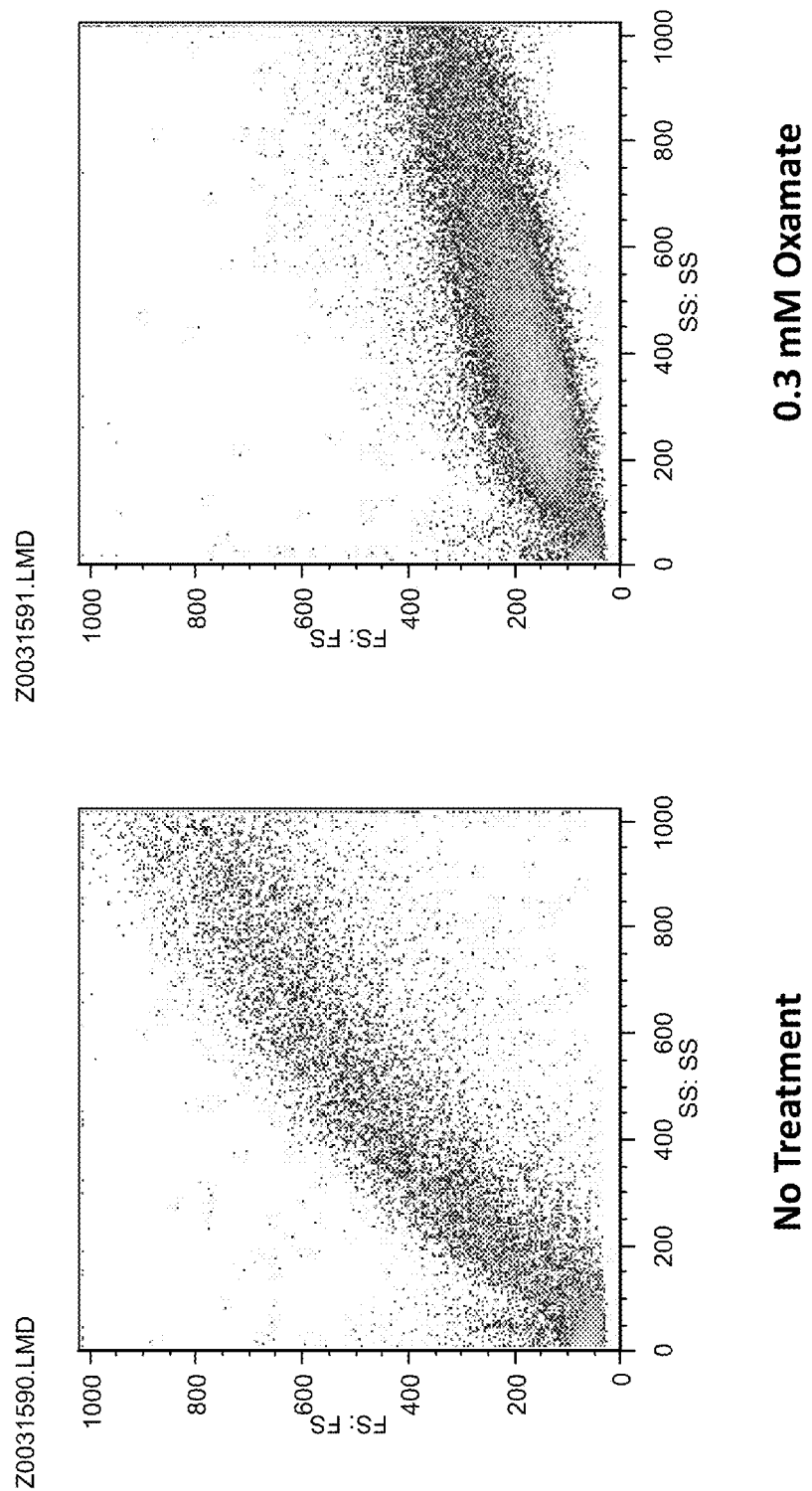
FIG. 4 is a set of dot plots of forward versus side scatter following treatment with 0.3 mM oxamate (FIG. 4A left panel) or untreated (FIG. 4A right panel) as an assessment for Oxamate-induced cell death. Decreased fsc and increased ssc indicate the cells have died apoptotically.
FIG. 4B is a dot plot of treated versus untreated within the same panel.

FIG. 4 is a set of dot plots of forward versus side scatter following treatment with 0.3 mM oxamate (FIG. 4A left panel) or untreated (FIG. 4A right panel) as an assesement for Oxamate-induced cell death. Decreased fsc and increased ssc indicate the cells have died apoptotically. FIG. 4B is a dot plot of treated versus untreated within the same panel.

Figure 5:
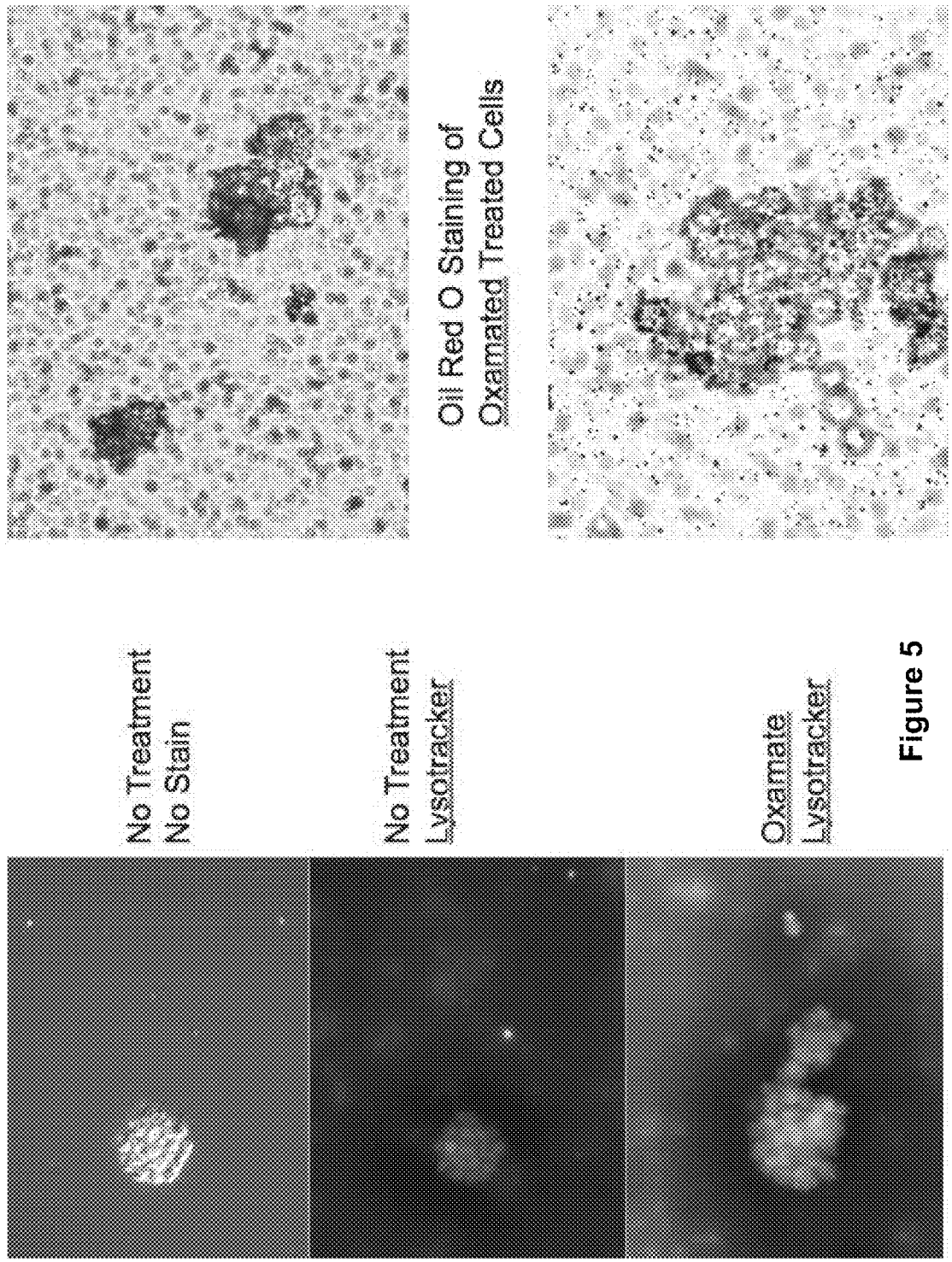
FIG. 5 is a set of photographs depicting *Schizochytrium* either treated with Oxamate or untreated as detected by lysosensor dye or oil red O staining. The left three panels depict the same cells with either no treatment on a gray scale (left, upper panel); no treatment but with fluorescence of Lysosensor dye (middle left panel) or Oxamate-treated *Schizochytrium*, fluorescence resulting from Lysosensor dye (bottom left panel). The right, upper panel depicts Oil Red O staining of untreated versus Oxamate-treated, *Schizochytrium* (right lower panel).

The cell morphology of the *Schizochytrium* were also examined and the fatty acids were observed using lysosensor dye and Oil Red O. FIG. 5 is a set of photographs depicting *Schizochytrium* either treated with oxamate or untreated as detected by lysosensor dye or oil red O statining. The left three panels depict the same cells with either no treatment on a gray scale (left, upper panel); no treatment but with fluorescence of Lysosensor dye (middle left panel) or Oxamate-treated *Schizochytrium*, fluorescence resulting from Lysosensor dye (bottom left panel). The right, upper panel depicts Oil Red O staining of untreated versus oxamate-treated, *Schizochytrium* (right lower panel). The oxamate treated cells show dramatically increased fat accumulation.

Example 2

Fatty Acid Accumulation in *Chlamydomonas reinhardtii*

Figure 6:
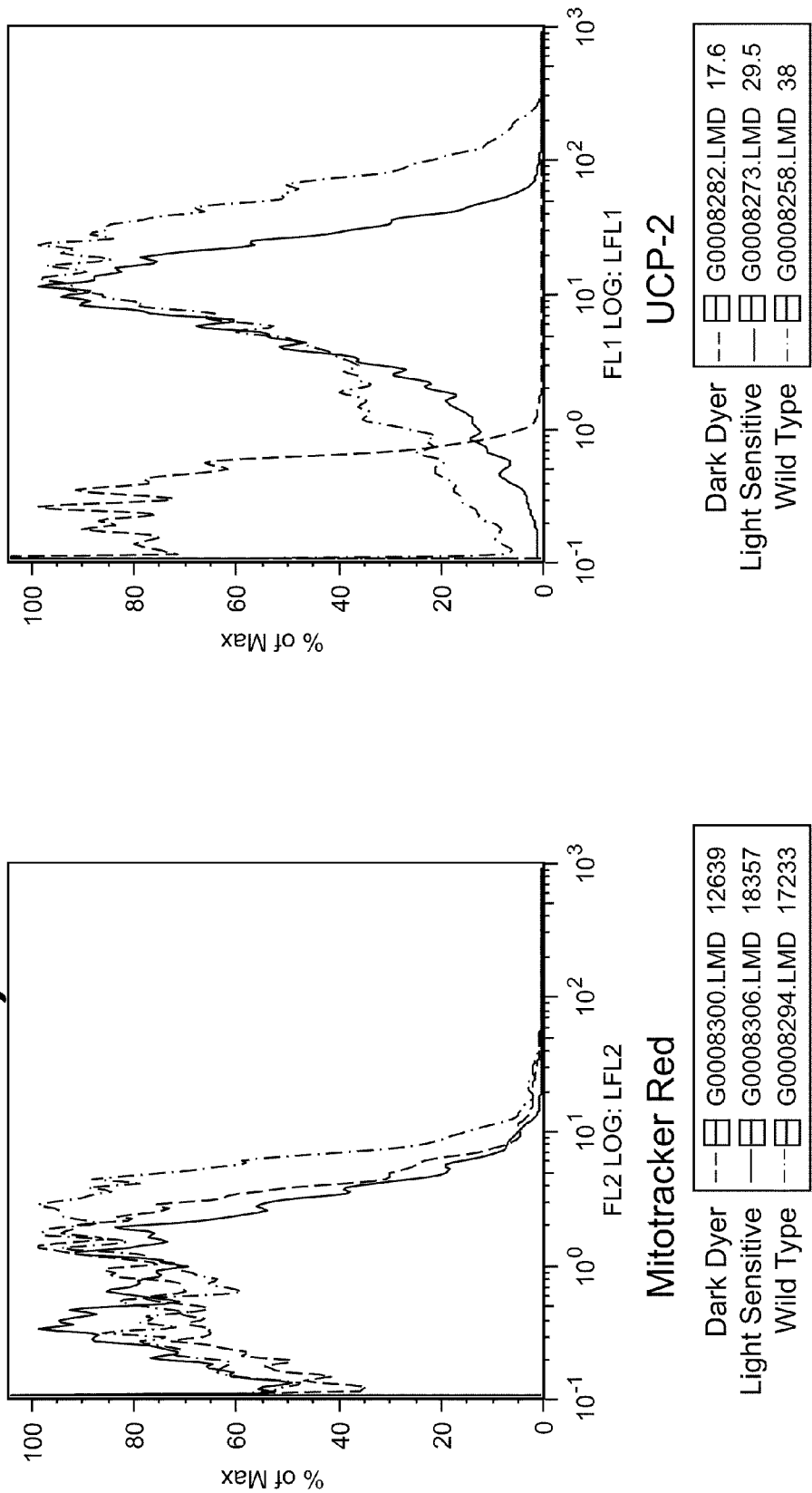
FIG. 6 is a set of histograms depicting mitochondrial membrane potential as measured by Mitotracker Red dye (left panel) or UCP-2 (right panel). The cells are wild type or mutant *Chlamydomonas* lines as indicated. Uncoupling proteins as detected by fluorochrome-conjugated anti-Uncoupling antibody as expressed on mutant and wild type lines of *Chlamydomonas* are shown in the right panel.

Increased fatty acid accumulation was also observed in the algae *Chlamydomonas*. FIG. 6 is a set of histograms depicting mitochondrial membrane potential as measured by Mitotracker Red dye (left panel) or UCP-2 (right panel). The cells are wild type or mutant *Chlamydomonas* lines as indicated. Uncoupling proteins as detected by fluorochrome-conjugated anti-Uncoupling antibody as expressed on mutant and wild type lines of *Chlamydomonas* are shown in the right panel.

Example 3

Nutrient Accumulation in Corn, Oat Cucumber and Pea

Figure 7:
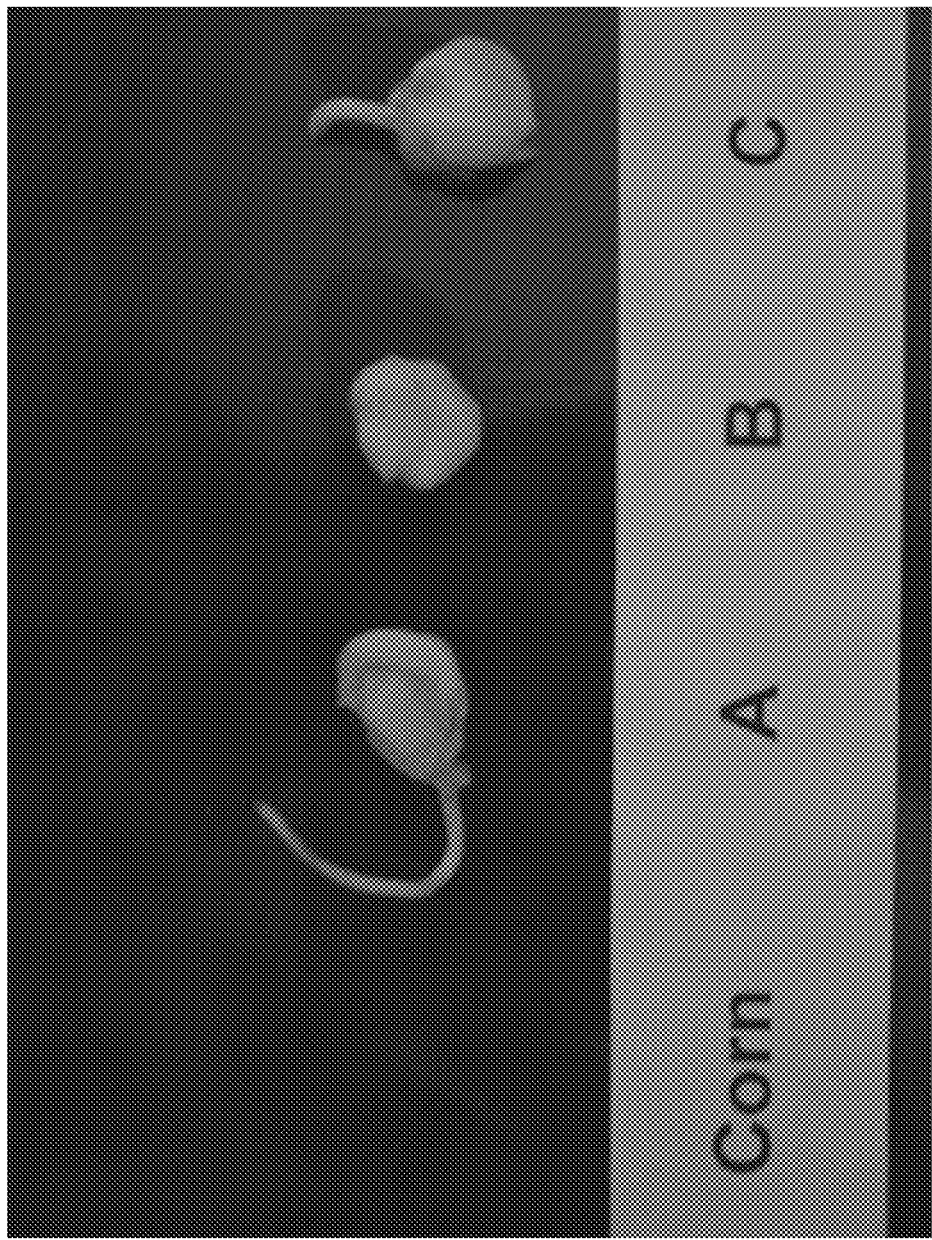
FIG. 7 is a photograph of corn seeds either treated with oxamate (B) or etomoxir (C) or untreated (A).
Figure 8:
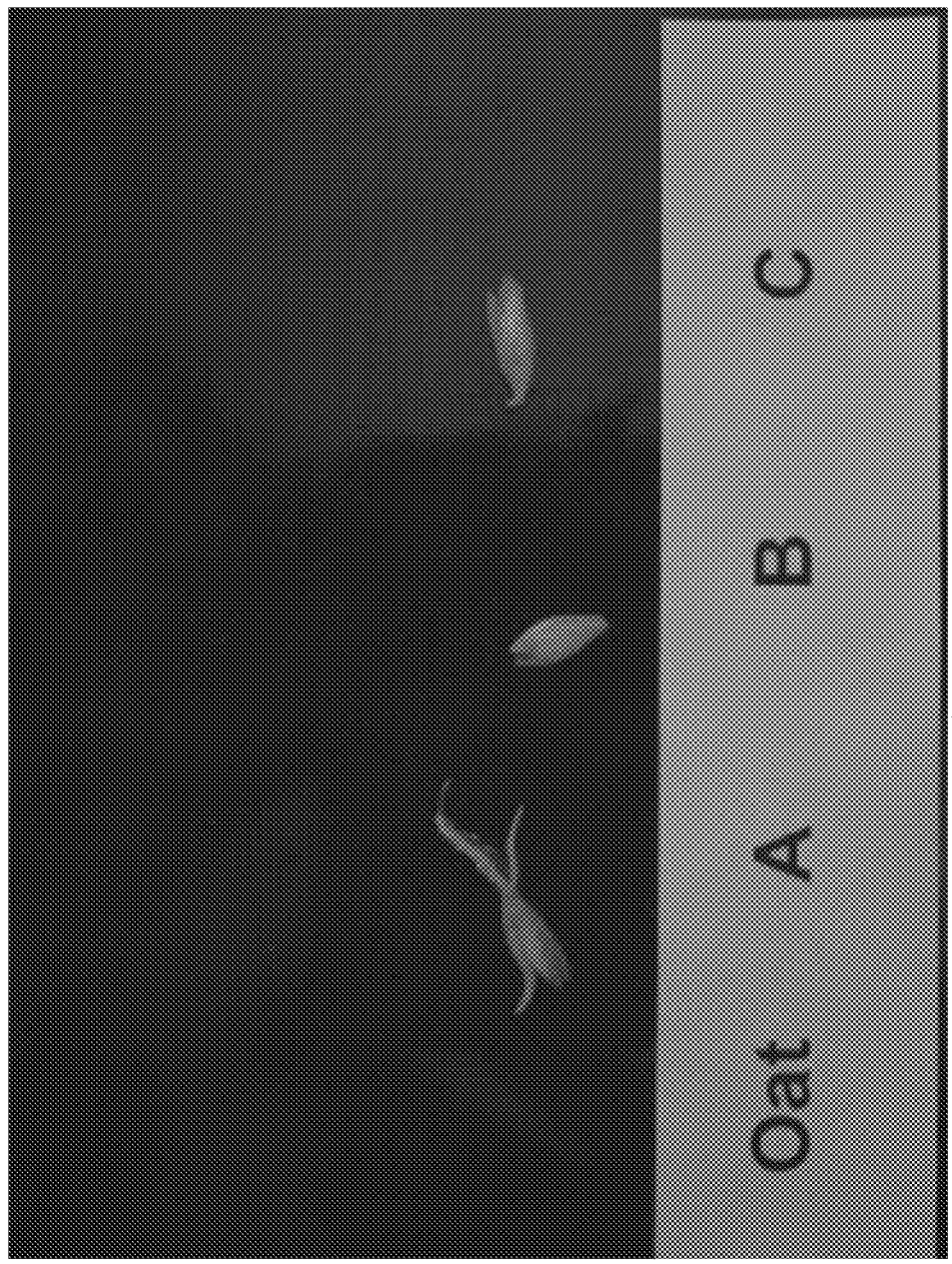
FIG. 8 is a photograph of oat seeds either treated with oxamate (B) or etomoxir (C) or untreated (A).
Figure 9:
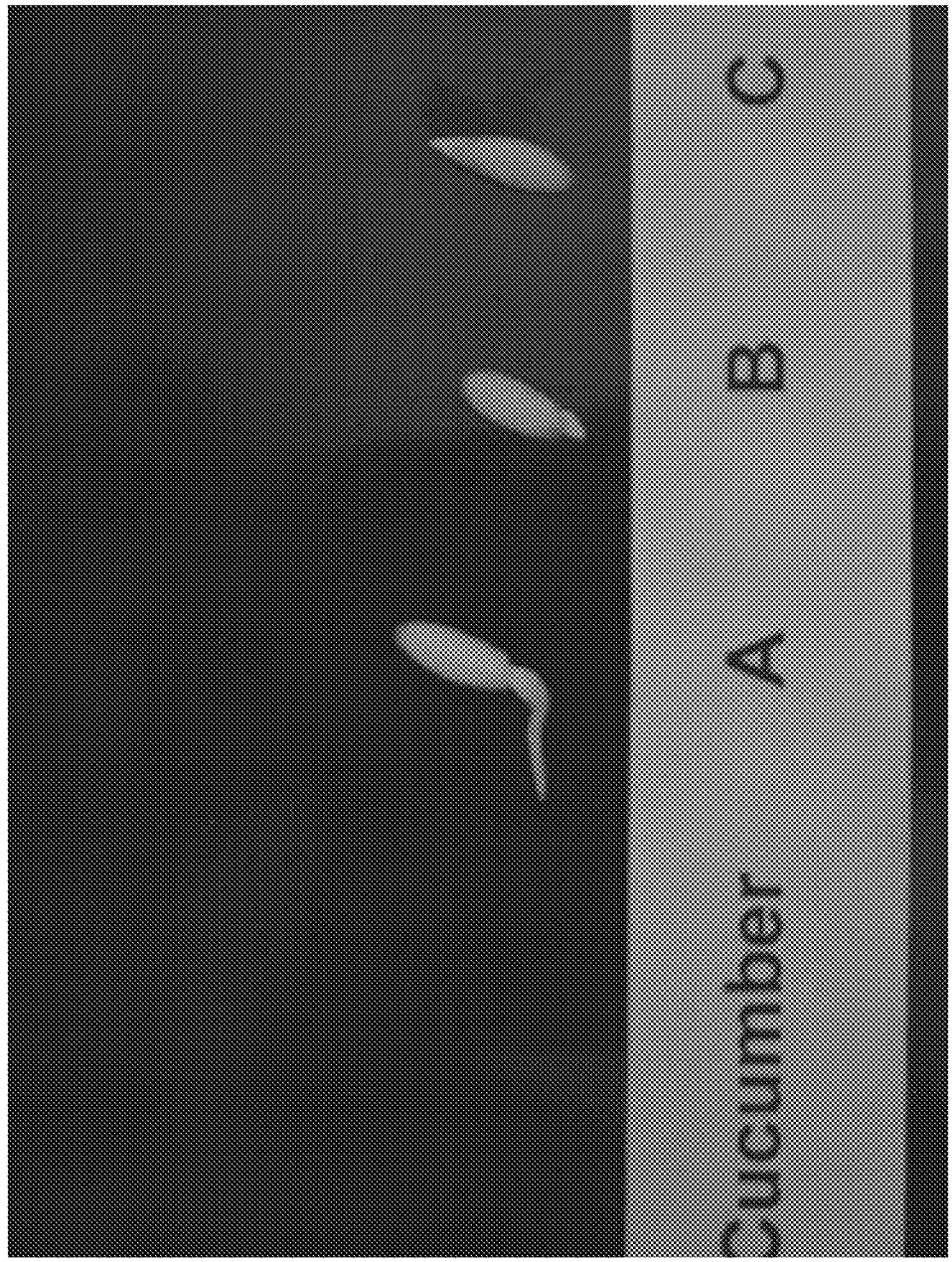
FIG. 9 is a photograph of cucumber seeds either treated with oxamate (B) or etomoxir (C) or untreated (A).
Figure 10:
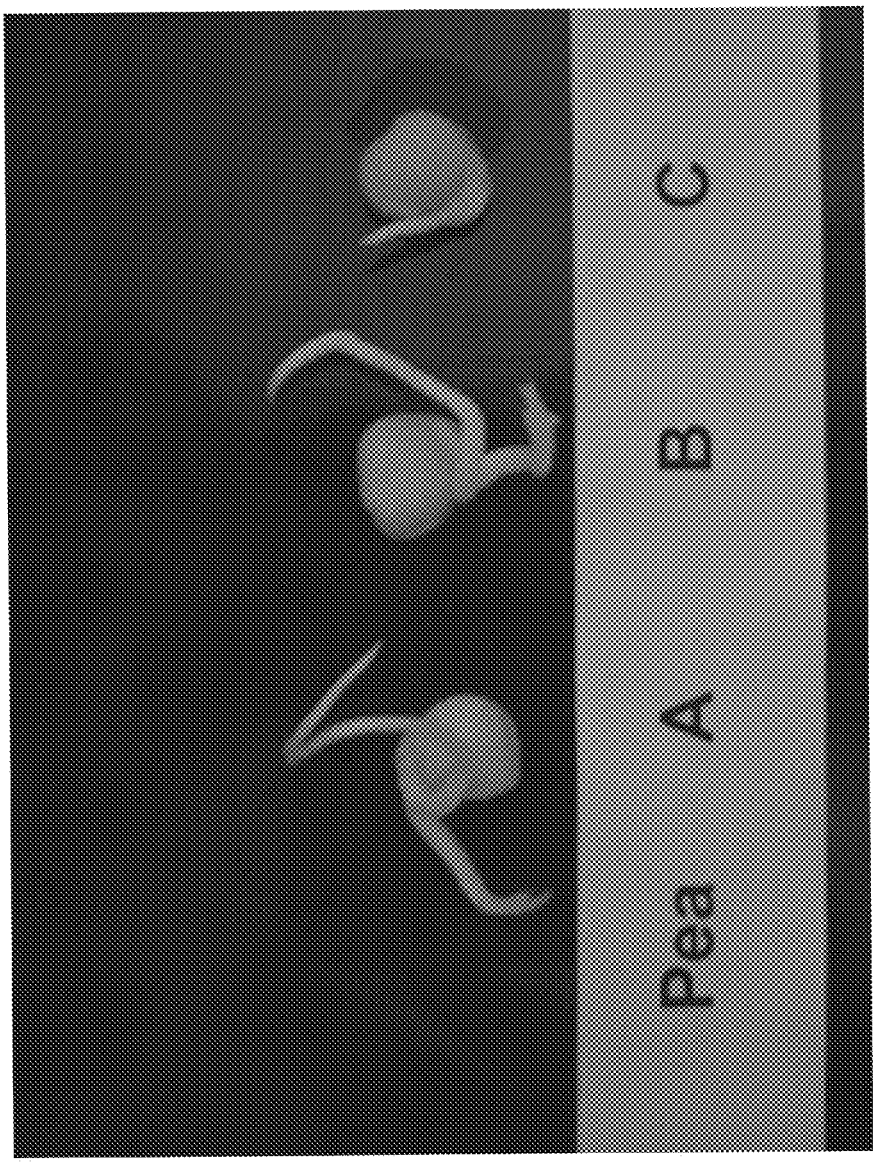
FIG. 10 is a photograph of pea seeds either treated with oxamate (B) or etomoxir (C) or untreated (A).

Seeds of corn, oat, cucumber and pea were treated with inhibitors of fatty acid oxidation and examined for accumulation of fatty acids as evidenced by lack of germination. FIG. 7 is a photograph of corn seeds either treated with oxamate (B) or etomoxir (C) or untreated (A). FIG. 8 is a photograph of oat seeds either treated with oxamate (B) or etomoxir (C) or untreated (A). FIG. 9 is a photograph of cucumber seeds either treated with oxamate (B) or etomoxir (C) or untreated (A). FIG. 10 is a photograph of pea seeds either treated with oxamate (B) or etomoxir (C) or untreated (A).

Prior Studies

Prior studies performed by some of the inventors relating to the manipulation of UCP in plants are described in U.S. Pat. No. 7,105,718 issued on Sep. 12, 2006. Those studies are set forth below as background information relating to the methods described herein. These are as follows.

Wild type (CC124, mt−) and cell wall-less (CC, mt+) *C. reinhardtii* were tested for the presence of UCP by flow cytometry. Non-permeabilized cells were stained with anti-UCP2 antibody (Santa Cruz Technologies). Cells were prepared for staining with goat anti-UCP2 antibody (Santa Cruz Pharmaceuticals) followed by fluorescein conjugated anti-rabbit or goat outer step antibodies, respectively. Cells were stained for intracellular peroxide using 6-carboxy-2'-7'-dichlorodihydrofluorescein diacetate (DCF-DA, Molecular Probes, Eugene, Oreg.). Briefly, cells were incubated with DCF-DA for 20 minutes, washed twice in PBS containing 5% fetal calf serum and analyzed flow cytometrically. Mitochondrial membrane potential was assessed using Mitotracker Red (CM-H2XROS, Molecular Probes, Eugene, Oreg.). The cells were resuspended in cold, or room temperature, PBS containing 13% fetal calf serum, 0.5 micromolar Mitotracker Red dye was then added to the suspension. The cells were incubated at 37° C. for 20 minutes, pelleted, and resuspended in prewarmed medium for analysis. The Coulter Excel flow cytometer was used with a single excitation wavelength (488 nm) and band filters for PE (575 nm), FITC (525 nm) and Red613 (613 nm) to analyze the stained cells. Each sample population was classified for cell size (forward scatter) and complexity (side scatter), gated on a population of interest and evaluated using 40,000 cells.

The data generated according to these methods illustrated that wild type (cell-walled [CC124−]), but not cell wall-less strains (cw15+) of *C. reinhardtii*, express cell surface molecules recognized by antibodies to UCP2. This result confirmed that UCP can be localized to the cell wall, in addition to mitochondria and chloroplast.

It had also been hypothesized that if cell wall expression of UCP2 facilitates uptake of acetate as an alternative carbon source during non-photosynthetic periods, then mutant strains of *C. reinhardtii* that die in the dark should not express cell wall UCP2. Such mutants were tested for the presence of cell wall UCP. It was found that light-sensitive, cell-walled strains of *C. reinhardtii* (its) expressed high levels of UCP. However, dark sensitive strains (CC2654; dark-dier) of *C. reinhardtii* expressed no cell-wall UCP over control samples. These results demonstrated a role of the cell wall UCP in non-photosynthetic metabolism.

It had been discovered that wild type strains of algae can be made light-sensitive in the presence of the herbicide norflurazon. Thus, it was reasoned, in view of those discoveries described above, that norflurazon upregulates cell wall expression of UCP. Algae made light-sensitive by treatment with norflurazon were tested for the presence of cell wall UCP. It was found that norflurazon did upregulate cell wall expression of UCP in wild type strains of *C. reinhardtii*. These experiments, when taken together, demonstrated that UCP functioned in *C. reinhardtii* when an alternative energy source to photosynthesis is required.

RNA from *C. reinhardtii* had also been examined. Total RNA was isolated from wild type, wild type treated with norflurazen, cell wall less CW15+, and light sensitive cells. Four concentrations of RNA were attached to the blot, 20 ug, 10 ug, 5 ug, and 2.5 ug. A 32P labeled probe from mouse clone in Bluescript was utilized. It was concluded that regulation of UCPs may be utilized to protect plants, tissues, or cells against free radical damage. These experiments demonstrated that UCP in *C. reinhardtii* cell walls protects against free radical damage. Specifically, *C. reinhardtii* was tested for changes in reactive oxygen levels flow cytometrically using DCF-DA (Molecular Probes, Eugene, Oreg.). It was reasoned that UCP functions to prevent increased levels of oxygen free radicals, thus, mitochondrial membrane potential was measured using Cm-CS ros (Molecular Probes, Eugene, Oreg.). The accuracy of this method for free radical quantification has been validated. The results demonstrated that UCP in *C. reinhardtii* protects against free radical damage.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

We claim:

1. A method for preparing a biofuel, comprising
   disrupting a fatty acid metabolism pathway in a plant cell or fungus, wherein the plant cell or fungus is an algae or schizochytrium, by contacting the plant cell or fungus with an inhibitor of fatty acid metabolism in an effective amount to promote accumulation or storage of fatty acids, wherein the inhibitor of fatty acid metabolism is oxamate,
   collecting the fatty acids from the plant cell or fungus, and
   processing the fatty acids to produce a biofuel.
2. The method of claim 1, wherein the biofuel is syngas.
3. The method of claim 2, wherein the syngas is processed by a Fischer-Tropsch reaction to produce a biodiesel.
4. The method of claim 1, wherein the biofuel is biodiesel.
5. The method of claim 4, wherein the biodiesel is processed using a transesterification process.
6. The method of claim 5, wherein the transesterification process is achieved by mixing the fatty acids with methanol.
7. The method of claim 1, wherein the fatty acids are processed to produce biofuel using a thermochemical liquification process.
8. The method of claim 1, wherein the fatty acids are processed to produce biofuel using a pyrolysis process.
9. The method of claim 1, wherein the plant cell or fungus is an algae.
10. The method of claim 1 wherein the disruption of the fatty acid metabolism pathway further comprises contacting the plant cell or fungus with a glycolytic inhibitor.
11. The method of claim 10, wherein the glycolytic inhibitor is a 2-deoxyglucose compound.
12. A method for producing fatty acids, comprising
    disrupting a fatty acid metabolism pathway in a plant cell or fungus, wherein the plant cell or fungus is an algae or schizochytrium, by contacting the plant cell or fungus with an inhibitor of fatty acid metabolism in an effective amount to promote accumulation or storage of fatty acids, and collecting the fatty acids as a source of biofuel, wherein the inhibitor of fatty acid metabolism is oxamate.
13. A method for producing a syngas, comprising disrupting a fatty acid metabolism pathway in a plant cell or fungus, wherein the plant cell or fungus is an algae or schizochytrium, by contacting the plant cell or fungus with oxamate in an effective amount to promote accumulation or storage of fatty acids, subjecting the plant cell or fungus to a gasification process and collecting syngas produced by the gasification process.

* * * * *